United States Patent
Weisburg et al.

(10) Patent No.: US 6,534,273 B2
(45) Date of Patent: *Mar. 18, 2003

(54) TWO-STEP HYBRIDIZATION AND CAPTURE OF A POLYNUCLEOTIDE

(75) Inventors: William G. Weisburg, San Diego, CA (US); Jay H. Shaw, San Diego, CA (US); Michael M. Becker, San Diego, CA (US); Mehrdad R. Majlessi, Escondido, CA (US); Steven T. Brentano, Santee, CA (US); Kiyotada Nunomura, Nishi-Tokyo (JP)

(73) Assignee: Gen-Probe Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/956,412

(22) Filed: Sep. 18, 2001

(65) Prior Publication Data

US 2002/0127569 A1 Sep. 12, 2002

Related U.S. Application Data

(60) Continuation-in-part of application No. 09/910,635, filed on Jul. 20, 2001, which is a division of application No. 09/574,561, filed on May 19, 2000, now Pat. No. 6,280,952, which is a division of application No. 09/070,998, filed on May 1, 1998, now Pat. No. 6,110,678
(60) Provisional application No. 60/045,430, filed on May 2, 1997.

(51) Int. Cl.$^7$ .................................................. C12Q 1/68
(52) U.S. Cl. ..................... 435/6; 536/23.1; 536/24.3; 435/91.2
(58) Field of Search ................... 435/6, 91.2; 536/23.1, 536/24.3

(56) References Cited

U.S. PATENT DOCUMENTS

| | | |
|---|---|---|
| 4,486,539 A | 12/1984 | Ranki et al. |
| 4,554,088 A | 11/1985 | Whitehead et al. |
| 4,581,333 A | 4/1986 | Kourilsky et al. |
| 4,683,195 A | 7/1987 | Mullis et al. |
| 4,751,177 A | 6/1988 | Stabinsky |
| 4,755,458 A | 7/1988 | Rabbani et al. |
| 4,868,105 A | 9/1989 | Urdea et al. |
| 4,882,269 A | 11/1989 | Schneider et al. |
| 4,894,325 A | 1/1990 | Englehardt et al. |
| 5,043,272 A | 8/1991 | Hartley |
| 5,112,734 A | 5/1992 | Kramer et al. |
| 5,124,246 A | 6/1992 | Urdea et al. |
| 5,130,238 A | 7/1992 | Malek et al. |
| 5,200,314 A | 4/1993 | Urdea et al. |
| 5,252,723 A | 10/1993 | Bhatt et al. |
| 5,273,882 A | 12/1993 | Snitman et al. |
| 5,283,174 A | 2/1994 | Arnold, Jr. et al. |
| 5,288,609 A | 2/1994 | Englehardt et al. |
| 5,399,491 A | 3/1995 | Kacian et al. |
| 5,437,990 A | 8/1995 | Burg et al. |
| 5,468,613 A | 11/1995 | Erlich et al. |
| 5,547,842 A | 8/1996 | Hogan et al. |
| 5,554,516 A | 9/1996 | Kacian et al. |
| 5,594,123 A | 1/1997 | Sninsky et al. |
| 5,635,352 A | 6/1997 | Urdea |
| 5,639,604 A | 6/1997 | Arnold et al. |
| 5,656,207 A | 8/1997 | Woodhead et al. |
| 5,658,737 A | 8/1997 | Nelson et al. |
| 5,702,896 A | 12/1997 | Collins et al. |
| 5,731,148 A | 3/1998 | Becker et al. |
| 5,731,153 A | 3/1998 | Lucas et al. |
| 5,750,338 A | 5/1998 | Collins et al. |
| 6,060,246 A | 5/2000 | Summerton et al. |
| 6,110,678 A | 8/2000 | Weisburg et al. |
| 6,133,436 A | 10/2000 | Koster et al. |
| 6,280,952 B1 | 8/2001 | Weisburg et al. |

FOREIGN PATENT DOCUMENTS

| | | |
|---|---|---|
| EP | 0149565 B1 | 7/1985 |
| EP | 0159719 A2 | 10/1985 |
| EP | 0265244 B1 | 4/1988 |
| EP | 0328829 A2 | 8/1989 |
| EP | 0370694 A2 | 5/1990 |
| EP | 0435150 A2 | 7/1991 |
| EP | 0444120 B1 | 9/1991 |
| EP | 0446260 B1 | 9/1991 |
| EP | 0454461 B1 | 10/1991 |
| EP | 0526912 A2 | 2/1993 |
| WO | WO 8504674 A1 | 10/1985 |
| WO | WO 8801302 A1 | 2/1988 |
| WO | WO 8810315 A1 | 12/1988 |
| WO | WO 8910979 A1 | 11/1989 |
| WO | WO 9010716 A1 | 9/1990 |
| WO | WO 9108307 A1 | 6/1991 |
| WO | WO 9114788 A1 | 10/1991 |
| WO | WO 9403472 A1 | 2/1994 |
| WO | WO 9419023 A1 | 9/1994 |
| WO | WO 9503430 A1 | 2/1995 |
| WO | WO 9516055 A1 | 6/1995 |

OTHER PUBLICATIONS

Albretsen et al., "Applications of Magnetic Beads with Covalently Attached Oligonucleotides in Hybridization:Isolation and Detection of Specific Measles virus mRNA from a Crude Cell Lysate" (1990) Anal. Biochem, 189:40–50.

(List continued on next page.)

Primary Examiner—Ethan C. Whisenant
(74) Attorney, Agent, or Firm—Christine A. Gritzmacher

(57) ABSTRACT

A method for capturing a target polynucleotide in a sample onto a solid support with an attached immobilized probe by using a capture probe and two different hybridization conditions that control the order of hybridization, where the first hybridization condition allows hybridization of the capture probe to the target polynucleotide, and the second hybridization condition allows hybridization of the capture probe to the immobilized probe. The method further includes amplifying the captured target polynucleotide by hybridizing at least one primer oligonucleotide to the target polynucleotide and using nucleic acid amplification that initiates from the primer oligonucleotide.

20 Claims, 7 Drawing Sheets

OTHER PUBLICATIONS

Arnold et al., "Assay Formats Involving Arcidinium–Ester–Labeled DNA Probes" (1989) Clin. Chem., 35(8):1588–1594.

Arsenyan et al., "Isolation of rat liver 5S RNA genes" (1980) Gene, 11:97–108.

Boom et al., "Rapid and Simple Method for Purification of Nucleic Acids" (1990) J. Clin. Microbiol., 28(3):495–503.

Brown et al., "Methods of Gene Isolation" (1974) Ann. Rev. Biochem., 43:667–693.

Brown, "Some Genes Were Isolated and Their Structure Studied Before the Recombinant DNA Era" (1994) Bio Essays, 16(2):139–143.

Buffone et al., "Improved Amplification of Cytomegalovirus DNA from Urine after Purfication of DNA with Glass Beads" (1991) Clin. Chem., 37(11):1945–1949.

Bunemann et al., "Hybrid Selection of Specific RNAs Using DNA Covalently Coupled to Macroporous Supports" (1983) Meth. Enzymol., 100(27):400–407.

Gaubatz et al., "Displacement synthesis of globin complementary DNA:evidence for sequence amplification" (1985) Biochem. Biophys. ACTA, 825:175–187.

Gillespie et al., "Probes for quantitating subpicogram amounts of HIV–1 RNA by molecular hybridization" (1989) Mol. Cell Probes, 3:73–86.

Goldkorn et al., "A simple and efficient enzymatic method for covalent attachment of DNA to cellulose. Application for hybridization—restriction analysis and for in vitro synthesis of DNA probes" (1986) Nuc. Acids Res., 14(22):9171–9191.

Harding et al., "Rapid isolation of DNA from complex biological samples using a novel capture reagent–methidium–spermine–sepharose" (1989) Nucleic Acids Res., 17(17):6947–6958.

Higuchi "Simple and Rapid Preparation of Samples for PCR" (1989) PCR Technology (Erlich, ed., Stockton Press, New York, NY), Chpt. 4, pp. 31–38.

Houghton et al., "The amino–terminal sequence of human fibroblast interferon as deduced from reverse transcripts obtained using synthetic oligonucleotide primers" (1980) Nucleic Acids Res., 8(9):1913–1931.

Impraim et al., "Analysis of DNA Extracted from Formalin–fixed, Paraffin–embedded Tissues By Enzymatic Amplification and Hybridization with Sequence–Specific Oligonucleotides" (1987) Biochem. Biophys. Res. Comm., 142(3):710–716.

Iwen et al., "Evaluation of Nucleic Acid–Based Test (PACE 2C) for Simultaneous Detection of Chlamydia trachomatis and Neisseria gonorrhoeae in Endocervical Specimens" (1995) J. Clin. Microbiol., 33(10):2587–2591.

Jovin et al., "Polynucleotide Cellulose as Solid State Primers and Templates for Polymerases" (1968) J. Biol. Chem., 243(2):250–259.

Jungell–Nortamo et al., "Nucleic acid sandwich hybridization:enhanced reaction rate with magnetic microparticles as carriers" (1988) Mol. Cell. Probes, 2:281–288.

Langdale et al., "Magnetic DNA" (1984) Biochem. Soc. Trans., 12:693–694.

Longacre et al., "Purification of Specific DNA Sequences by Sulfhydryl–Sepharose Chromatography of Mercurated Polynucleotides" (1973) J. Biol. Chem., 253(20):7500–7507.

Lund et al., "Assessment of Methods for Covalent Binding of Nucleic Acids to Magnetic Beads, Dynabeads™, and the Characteristics of the Bound Nucleic Acids in Hybridization Reactions" (1988) Nucleic Acids Res., 16(22):10861–10880.

McGrogan et al., "Purification of specific adenovirus 2 RNAs by preparative hybridization and selective thermal elution" (1979) Nucleic Acids Res., 6(2):593–607.

Moore et al., "Amplification of rRNA for Assessment of Treatment Response of Pulmonary Tuberculosis Patients during Antimicrobial Therapy" (1996) J. Clin. Microbiology, 34(7):1745–1749.

Morrissey et al., "Nucleic Acid Hybridization Assays Employing dA–Tailed Capture Probes" (1989) Anal. Biochem., 181:345–359.

Nelson et al., "Detection of all Single–Base Mismatches in Solution by Chemiluminescence" (1996) Nucleic Acids Res., 24(24):4998–5003.

Nelson et al., "Simultaneous Detection of Multiple Nucleic Acid Targets in a Homogeneous Format" (1996) Biochemistry, 35(25):8429–8438.

Ohara et al., "One–sided polymerase chain reaction:The amplification of cDNA" (1989) Proc. Natl. Acad. Sci. USA, 86:5673–5677.

Panet et al., "Studies on Polynucleotides—The Linkage of Deoxyribopolynucleotide Templates to Cellulose and its use in Their Replication" (1974) J. Biol. Chem., 249(16):5213–5221.

Polsky–Cynkin et al., "Use of DNA Immobilized on Plastic and Agarose Supports to Detect DNA by Sandwich Hybridization" (1985) Clin. Chem., 31(9):1438–1443.

Ryskov et al., "Short Communication—Purification of Large Native DNA Fragments Enriched in Globin Gene Sequences" (1978) Gene, 3:81–85.

Sambrook et al., Molecular Cloning—A Laboratory Manual, 2nd Ed. (1989), vol. 1, Chpt. 1, §1.90–1.91, "Plasmid Vectors"; and Chpt. 7, §7.37–7.57, "Extraction, Purification, and Analysis of Messenger RNA from Eukaryotic Cells" (Cold Spring Harbor Laboratory Press, Plainview, NY).

Sambrook et al., Molecular Cloning—A Laboratory Manual, 2nd Ed. (1989), vol. 2, Chpt. 9, §9.47–9.51, "Analysis and Cloning of Eukaryotic Genomic DNA"; Chpt. 10, §10.2–10.65, "Preparation of Radiolabeled DNA and RNA Probes"; and Chpt. 11, §11–47–11.57, "Synthetic Oligonucleotide Probes" (Cold Spring Harbor Laboratory Press, Plainview, NY).

Shih et al., "Chemical Linkage of Nucleic Acids to Neutral and Phosphorylated Cellulose Powders and Isolation of Specific Sequences by Affinity Chromatography" (1974) Biochemistry, 13(16):3411–3417.

Syvanen, "Nucleic Acid Hybridizaton:From Research Tool To Routine Diagnostic Method" (1986) Med. Biol., 64:313–324.

Thompson et al., "Enzymatic Amplification of RNA Purified from Crude Cell Lysate by Reversible Target" (1989) Clin. Chem., 35(9):1878–1881.

Thrash et al., "Synthesis of RNA from Cellulose–bound Complementary DNA" (1977) J. Biol. Chem., 252(16):5615–5618.

Urdea et al., "A novel method for the rapid detection of specific nucleotide sequences in crude biological samples without blotting or radioactivity; application to the analysis of hepatitis B virus in human serum" (1987) Gene, 61(3):253–264.

Venetianer et al., "Enzymatic Synthesis of Solid Phase-–Bound DNA Sequences Corresponding to Specific Mammalian Genes" (1974) Proc. Natl. Acad. Sci., 71(10):3892–3895.

Von Eggeling et al., "Applications of Random PCR" (1995) Cell. Mol. Biol., 41(5):653–670.

Welcher et al., "Selective enrichment of specific DNA, cDNA and RNA sequences using biotinylated probes, avidin and copper–chelate agarose" (1986) Nucleic Acids Res., 14(24):10027–10044.

Metmur et al., "DNA Probes: Applications of the Principles of Nucleic Acid Hybridization" (1991) Crit. Rev. Biochem. Molec. Biol., 26(3/4):227–259.

Wittig et al., Cloning of chicken embryo tRNA genes using single stranded nucleosomal DNA highly enriched for tRNA complementary sequences (1979) Nucleic Acids Res., 6(12):3759–3772.

Woo et al., "The Ovalbumin Gene—Purification of the Anticoding Strand" (1977) J. Biol. Chem., 252(16):5789–5797.

Wood et al., "Purification of Biologically Active Globin mRNA Using cDNA–cellulose Affinity Chromatography" (1977) J. Biol. Chem., 252(2):457–463.

Disclosure from SISKA Diagnostics, Inc., San Diego, CA, May 27, 1987: "Siska Diagnostics' Nucleic Acid Probes" with Attachment 1 ("Siska Diagnostics' OligoProbeTM Oligonucleotide Probes for Viral Pathogens") and Attachment 2 ("Siska Diagnostics' OligoBeadsTM for Affinity Absorption for Nucleic Acids"); 9 pgs.-

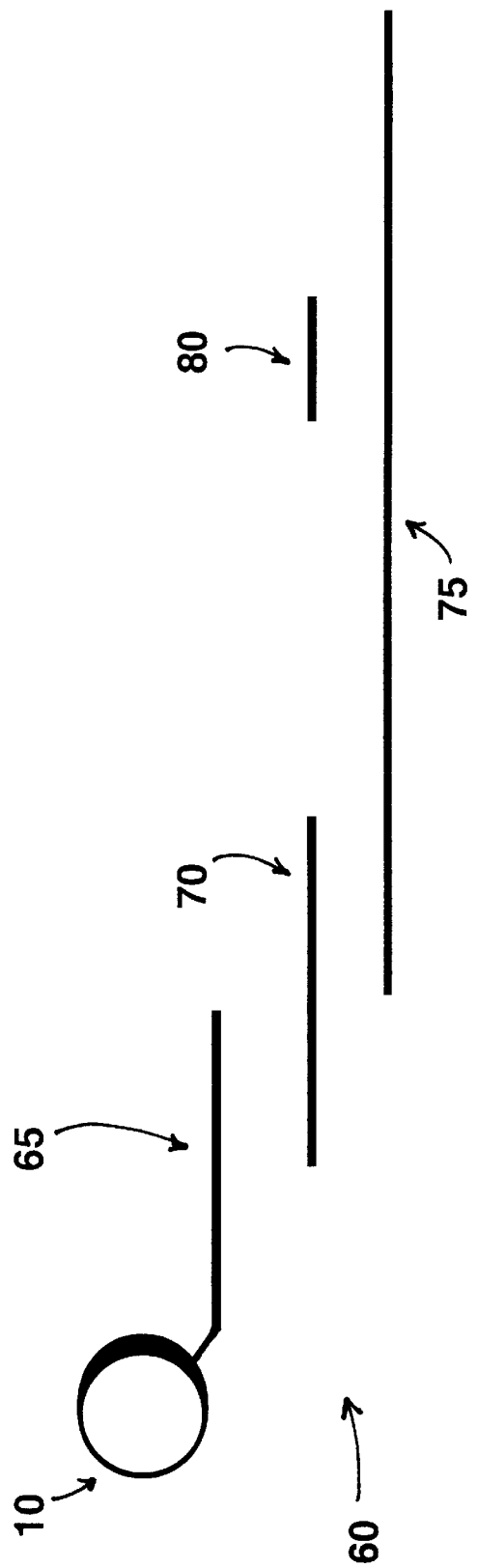

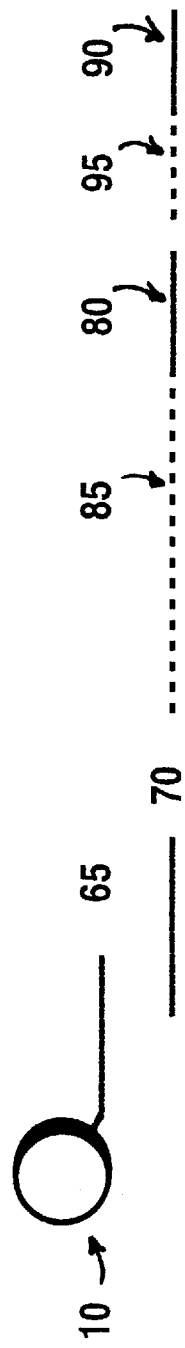
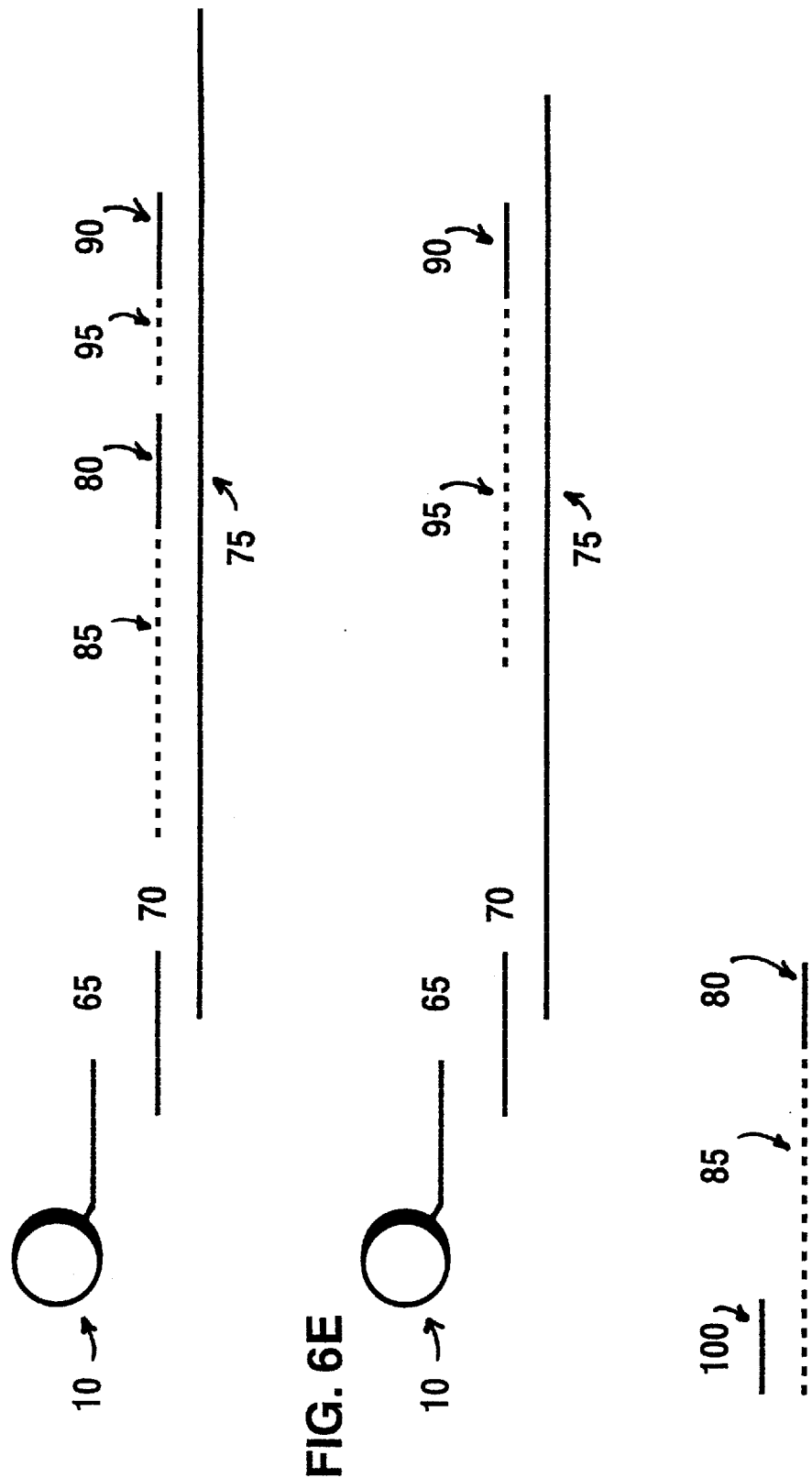
FIG. 6D
FIG. 6E

SEQUENCE LISTING

<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: capture probe oligonculeotide

<400> SEQUENCE: 1
gaactactta gttccaatga ctgtttaaaa aaaaaaaaaa                40

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:  target
      sequence complementary to a portion of the capture
      probe oligonucleotide

<400> SEQUENCE: 2
cagtcattgg aactaagtag ttc                                              23
```

TWO-STEP HYBRIDIZATION AND CAPTURE OF A POLYNUCLEOTIDE

RELATED APPLICATION

This application is a continuation in part of U.S. Ser. No. 09/910,635 filed Jul. 20, 2001, which is a divisional of U.S. Ser. No. 09/574,561 filed May 19, 2000, now U.S. Pat. No. 6,280,952, which is a divisional of U.S. Ser. No. 09/070,998 filed May 1, 1998, now U.S. Pat. No. 6,110,678 which claims the benefit under 35 U.S.C. § 119(e) of U.S. Ser. No. 60/045,430, filed May 2, 1997, now abandoned.

FIELD OF THE INVENTION

The present invention relates to methods for capturing a polynucleotide which may be present in a sample onto a solid support. The invention is particularly useful for separating a target polynucleotide from other material in a sample, and is preferably employed as part of a diagnostic procedure that included nucleic acid amplification to detect the presence of the target polynucleotide.

BACKGROUND OF THE INVENTION

A target polynucleotide is a polynucleotide present in a sample that can be purified from one or more sample components and/or whose presence can be detected using different techniques. Such techniques are typically carried out as part of a diagnostic procedure to detect the presence of a target polynucleotide which is indicative of the presence of an infectious agent or pathogenic condition.

The presence of a target polynucleotide base sequence region, present in a target polynucleotide, can be detected by various methods such as those using nucleic acid probes that hybridize to a target sequence. Probes can be designed to detect different target sequences such as those characteristic of microorganisms, viruses, human genes, plant or animal genes, and/or pathogenic conditions.

A technique for purifying a target polynucleotide, which is often used in diagnostic procedures, involves capturing a target polynucleotide onto a solid support. The solid support retains the target polynucleotide during one or more washing steps of the target polynucleotide purification procedure.

Ranki et al., U.S. Pat. No. 4,486,539 describe a hybridization sandwich technique for capturing and for detecting the presence of a target polynucleotide. The technique involves the capture of the target polynucleotide by a probe bound to a solid support and hybridization of a detection probe to the captured target polynucleotide. Detection probes not hybridized to the target polynucleotide are readily washed away from the solid support. Thus, remaining label is associated with the target polynucleotide initially present in the sample.

Stabinsky, U.S. Pat. No. 4,751,177 describes a method that uses a mediator polynucleotide that hybridizes to both a target polynucleotide and to a polynucleotide fixed on a solid support. The mediator polynucleotide joins the target polynucleotide to the solid support to produce a bound target. A labeled probe can be hybridized to the bound target and unbound labeled probe can be washed away from the solid support.

Englehardt et al., U.S. Pat. Nos. 4,894,324 and 5,288,609, describe a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

Cape et al., EP Pat. Pub. No. 0 370 694, describe methods and kits for detecting nucleic acids using a solid phase capture means. The methods use oligonucleotide primers labeled with specific binding partners to immobilize primers and primer extension products. The label specifically complexes with its receptor which is bound to a solid support.

SUMMARY OF THE INVENTION

According to one aspect of the invention, there is disclosed a method of capturing a target polynucleotide present in a sample. The method includes the steps of incubating a mixture comprising a target polynucleotide, a capture probe, and an immobilized probe in a first hybridization condition that favors formation of a capture probe:target hybridization complex that includes the capture probe and the target polynucleotide, wherein the first hybridization condition disfavors formation of an immobilized probe:capture probe hybridization complex that includes the immobilized probe and the capture probe; and then incubating the mixture in a second hybridization condition that favors formation of the immobilized probe:capture probe hybridization complex, thereby capturing the target polynucleotide in an immobilized probe:capture probe:target hybridization complex that includes the immobilized probe, the capture probe and the target polynucleotide. In one embodiment, the first incubating step uses a temperature below a $T_m$ of the capture probe:target hybridization complex and above a $T_m$ of the immobilization probe:capture probe hybridization complex, and the second incubating step uses a temperature below a $T_m$ of the immobilization probe:capture probe hybridization complex. Preferably, the second incubating step is achieved by lowering the temperature of the first hybridization condition by at least about 10° C., or by at least about 20° C. In one preferred embodiment the first incubating step uses a temperature of about 60° C. and the second incubating step uses a temperature of about 40° C. or lower. Alternatively, the first incubating step may use a solution having a chemical stringency that favors formation of the capture probe:target hybridization complex and disfavors formation of the immobilization probe:capture probe hybridization complex, and the second incubating step lowers the chemical stringency of the solution, thereby favoring formation of the immobilization probe:capture probe hybridization complex. One embodiment of the method also includes the step of purifying the immobilized probe:capture probe:target hybridization complex. Another embodiment includes the step of detecting the target polynucleotide in the purified immobilized probe:capture probe:target hybridization complex. Preferably, the detecting step comprises hybridizing a labeled probe to the target polynucleotide in the purified immobilized probe:capture probe:target hybridization complex. In another embodiment, the detecting step further includes removing the labeled probe that has not hybridized to the target polynucleotide. One embodiment of the method also includes the step of detecting the target polynucleotide in the immobilized probe:capture probe:target hybridization complex, preferably by hybridizing a labeled probe to the target polynucleotide. This embodiment may also include the step of removing the labeled probe that has not hybridized to the target polynucleotide. Another embodiment of the method includes the step of amplifying the target polynucleotide to produce an amplified nucleic acid. Preferably, the amplifying step is accomplished by transcription-associated amplification. This embodiment may further include the step of detecting the amplified nucleic acid. Preferably, the detecting step includes hybridizing a labeled probe to the amplified nucleic acid that has a sequence complementary to the target polynucleotide sequence, and may also include removing the labeled probe that has not hybridized to the amplified nucleic acid. In one embodiment of the method the immobilized probe includes a capture probe-binding region of at least five nucleotide base recognition groups in length, and the capture probe includes an immobilized probe-binding region of at least five nucleotide base recognition groups in length, provided that the capture probe-binding region is complementary to the immobilized probe-binding region. Preferably, the capture probe-binding region of the immobilized probe includes (a) a first backbone containing at least one sugar-phosphodiester linkage, or at least one peptide nucleic acid group, at least one phosphorothioate linkage, or a combination thereof, and (b) at least ten nucleotide base recognition groups joined to the first backbone, wherein each nucleotide base recognition group is capable of hydrogen bonding with adenine, guanine, cytosine, thymine, uracil or inosine; and the immobilized probe-binding region of the capture probe includes (a) a second backbone containing at least one sugar-phosphodiester linkage, or at least one peptide nucleic acid group, at least one phosphorothioate linkage, or a combination thereof, and (b) at least ten nucleotide base recognition groups joined to the second backbone, which are capable of hydrogen bonding to the nucleotide base recognition groups joined to the first backbone. In a preferred embodiment, the capture probe-binding region of the immobilized probe consists of a repetitious base sequence of at least 10 nucleotide base recognition groups, and the immobilized probe-binding region of the capture probe consists of a repetitious base sequence comprising at least 25 nucleotide base recognition groups, of which at least 10 nucleotide base recognition groups are complementary to the capture probe-binding region. In one embodiment, the capture probe-binding region includes a sequence of about fourteen contiguous A or T, and the immobilized probe-binding region includes a sequence of 30 bases complementary thereto. In the method, the capture probe and the immobilized probe may each be made up of deoxynucleotides, ribonucleotides, 2'-methoxy substituted nucleotides, 2'-halo substituted nucleotide components, or combinations thereof.

Another aspect of the invention is a method for determining the presence of a target polynucleotide in a sample. This method includes the steps of: providing a capture probe capable of hybridizing to a target polynucleotide present in a sample; mixing the capture probe with a sample suspected of containing the target polynucleotide at a first incubation temperature that favors hybridization of the capture probe and the target polynucleotide, thereby producing a capture probe:target polynucleotide complex; providing an immobilized probe capable of hybridizing to the capture probe; incubating a mixture comprising the capture probe:target polynucleotide complex and the immobilized probe at a second incubation temperature that favors hybridization of the immobilized probe and the capture probe, thereby producing a captured target polynucleotide comprising an immobilized probe:capture probe:target polynucleotide complex; purifying the captured target polynucleotide, thereby producing a purified target polynucleotide; amplifying the purified target polynucleotide, thereby producing an amplified nucleic acid; and detecting the amplified nucleic acid which indicates the presence of the target polynucleotide in the sample. In one embodiment, the detecting step detects an amplified nucleic acid that is complementary to the target polynucleotide or a portion thereof. Preferably, the detecting step comprises using a labeled probe to detect the amplified nucleic acid.

One aspect of the invention is a method for amplifying a target polynucleotide that is present in a sample that includes the steps of:

a. providing a capture probe that hybridizes specifically to a target polynucleotide present in a sample;

b. providing a first primer oligonucleotide that hybridizes specifically to the target polynucleotide at a location different than the location that the capture probe hybridizes to the target polynucleotide;

c. mixing the capture probe and the primer oligonucleotide with a sample suspected of containing the target polynucleotide at a first hybridization condition that favors hybridization of the capture probe to the target polynucleotide and the primer oligonucleotide to the target polynucleotide, thereby producing a capture probe:target polynucleotide:primer oligonucleotide complex formed by hybridization of the capture probe and the primer oligonucleotide to the target polynucleotide, wherein the first hybridization condition disfavors hybridization of an immobilized probe and the capture probe;

d. providing an immobilized probe that hybridizes specifically to the capture probe at a second hybridization condition that is different from the first hybridization condition;

e. incubating a mixture containing the capture probe:target polynucleotide:primer oligonucleotide complex and the immobilized probe at a second hybridization condition that favors hybridization of the immobilized probe and the capture probe, thereby producing a captured target polynucleotide complex consisting essentially of an immobilized probe:capture probe:target polynucleotide:primer oligonucleotide complex formed by hybridization of the immobilized probe to the capture probe in the capture probe:target polynucleotide:primer oligonucleotide complex;

f. purifying the captured target polynucleotide complex from other sample components by washing the captured target polynucleotide complex, thereby producing a purified target polynucleotide retained in the immobilized probe:capture probe:target polynucleotide:primer oligonucleotide complex; and g. then amplifying a base sequence in the target polynucleotide by initiating nucleic acid polymerization from the first primer oligonucleotide using the target polynucleotide as a template and a DNA polymerase activity, thereby producing an amplified nucleic acid. In one embodiment, the first hybridization condition uses an incubation temperature below a $T_m$ of the capture probe:target polynucleotide hybridization complex and above a $T_m$ of the immobilized probe:capture probe hybridization complex, and the second hybridization condition uses an incubation temperature below a $T_m$ of the immobilized probe:capture probe hybridization complex. Another embodiment includes in the amplifying step hybridizing a second primer oligonucleotide to the target polynucleotide upstream of the first primer oligonucleotide hybridized to the target polynucleotide, and polymerizing a first complementary nucleic acid strand initiating from the first primer oligonucleotide and a second complementary nucleic acid strand initiating from the second primer oligonucleotide, both complementary nucleic acid strands polymerized using the same strand of the target polynucleotide as a template. In one embodiment, the second complementary nucleic acid strand displaces the first complementary nucleic acid strand from the target polynucleotide. In the method, the DNA polymerase activity may be provided by a reverse transcriptase and the first primer oligonucleotide may be a promoter primer. In a preferred embodiment, hybridization of the capture probe to the target polynucleotide and hybridization of the primer oligonucleotide to the target polynucleotide occurs in liquid phase. In one embodiment, the amplifying step initiates polymerization from the first primer oligonucleotide hybridized to the target polynucleotide without releasing the target polynucleotide from the immobilized probe:capture probe:target polynucleotide:primer oligonucleotide complex.

Another aspect of the invention is a method for amplifying a target polynucleotide that is present in a sample, that includes the steps of:

a. providing a capture probe that hybridizes specifically to a target polynucleotide present in a sample;

b. providing a first primer oligonucleotide that hybridizes specifically to the target polynucleotide at a location different than the location that the capture probe hybridizes to the target polynucleotide;

c. mixing the capture probe and the primer oligonucleotide with a sample suspected of containing the target polynucleotide at a first hybridization condition that favors hybridization of the capture probe and the target polynucleotide, thereby producing a capture probe:target polynucleotide:primer oligonucleotide complex formed by hybridization of the capture probe and the primer oligonucleotide to the target polynucleotide, wherein the first hybridization condition disfavors hybridization of an immobilized probe and the capture probe and disfavors hybridization of the primer oligonucleotide to the target polynucleotide;

d. providing an immobilized probe that hybridizes specifically to the capture probe at a second hybridization condition that is different from the first hybridization condition;

e. incubating a mixture containing the capture probe:target polynucleotide complex and the primer oligonucleotide and immobilized probe at a second hybridization condition that favors hybridization of the immobilized probe with the capture probe and the primer oligonucleotide with the target polynucleotide, thereby producing a captured target polynucleotide complex consisting essentially of an immobilized probe:capture probe:target polynucleotide:primer oligonucleotide complex formed by hybridization of the immobilized probe with the capture probe which is hybridized with the target polynucleotide and the primer oligonucleotide with the target polynucleotide which is hybridized to the capture probe;

f. purifying the captured target polynucleotide complex from other sample components by washing the captured target polynucleotide complex, thereby producing a purified target polynucleotide retained in the immobilized probe:capture probe:target polynucleotide:primer oligonucleotide complex; and g. then amplifying a base sequence in the target polynucleotide by initiating nucleic acid polymerization from the first primer oligonucleotide using the target polynucleotide as a template and a DNA polymerase activity, thereby producing an amplified nucleic acid. In one embodiment of this method, the first hybridization condition uses an incubation temperature below a $T_m$ of the capture probe:target polynucleotide hybridization complex and above a $T_m$ of the immobilized probe:capture probe hybridization complex, and the second hybridization condition uses an incubation temperature below a $T_m$ of the immobilized probe:capture probe hybridization complex. In one embodiment of the method, the amplifying step also hybridizes a second primer oligonucleotide to the target polynucleotide upstream of the first primer oligonucleotide hybridized to the target polynucleotide, and polymerizes a first complementary nucleic acid strand initiating from the first primer oligonucleotide and a second complementary nucleic acid strand initiating from the second primer oligonucleotide, both complementary nucleic acid strands polymerized using the same strand of the target polynucleotide as a template. The second complementary nucleic acid strand can displace the first complementary nucleic acid strand from the target polynucleotide. In a preferred embodiment, the DNA polymerase activity is provided by a reverse transcriptase. In one embodiment, the first primer oligonucleotide is a promoter primer. In another embodiment, the amplifying step initiates polymerization from the first primer oligonucleotide hybridized to the target polynucleotide without releasing the target polynucleotide from the immobilized probe:capture probe:target polynucleotide:primer oligonucleotide complex.

Another aspect of the invention is a method for detecting the presence of a target polynucleotide in a sample, that includes the following steps:

a. providing a capture probe that hybridizes specifically to a target polynucleotide present in a sample;

b. providing a first primer oligonucleotide that hybridizes specifically to the target polynucleotide at a location different than the location that the capture probe hybridizes to the target polynucleotide;

c. mixing the capture probe and the primer oligonucleotide with a sample suspected of containing the target polynucleotide to produce a mixture;

d. incubating the mixture at a first hybridization condition that favors hybridization of the capture probe to the target polynucleotide, thereby producing a capture probe:target polynucleotide complex formed by hybridization of the capture probe and the primer oligonucleotide to the target polynucleotide, wherein the first hybridization condition optionally favors hybridization of the primer oligonucleotide to the target polynucleotide and disfavors hybridization of an immobilized probe and the capture probe;

e. providing an immobilized probe that hybridizes specifically to the capture probe at a second hybridization condition that is different from the first hybridization condition;

f. incubating a mixture containing the capture probe:target polynucleotide complex and the immobilized probe at a second hybridization condition that favors hybridization of the immobilized probe and the capture probe and favors hybridization of the primer oligonucleotide with the target polynucleotide, thereby producing a captured target polynucleotide complex consisting essentially of an immobilized probe:capture probe:target polynucleotide:primer oligonucleotide complex formed by hybridization of the immobilized probe to the capture probe in the capture probe:target polynucleotide complex and the capture probe:target polynucleotide:primer oligonucleotide complex;

g. purifying the captured target polynucleotide complex from other sample components by washing the captured target polynucleotide complex, thereby producing a purified target polynucleotide retained in the immobilized probe:capture probe:target polynucleotide:primer oligonucleotide complex;

h. then amplifying a base sequence in the target polynucleotide by initiating nucleic acid polymerization from the first primer oligonucleotide using the target polynucleotide as a template and a DNA polymerase activity, thereby producing an amplified nucleic acid; and i. detecting the amplified nucleic acid which indicates the presence of the target polynucleotide in the sample. In one embodiment, the detecting step detects an amplified nucleic acid that is complementary to a sequence in the target polynucleotide. Another embodiment uses a labeled probe to detect the amplified nucleic acid in a homogeneous detection method. In a preferred embodiment, the capture probe is an oligonucleotide containing a target polynucleotide-binding region that is substantially complementary to a sequence in the target polynucleotide, and an immobilized probe-binding region that is substantially complementary to the immobilized probe. One preferred embodiment, in the amplifying step, uses a transcription-associated amplification in which a reverse transcriptase acts together with the first primer oligonucleotide which is a promoter-primer to form a DNA duplex specific for the target polynucleotide and containing a double-stranded promoter, and then an RNA polymerase recognizes the double-stranded promoter to generate multiple RNA transcripts specific for the target polynucleotide, thereby producing the amplified nucleic acid.

BRIEF DESCRIPTION OF THE DRAWINGS

In FIG. 1A, the first hybridization condition permits hybridization of capture probe (b) and target polynucleotide (c) to form a capture probe:target polynucleotide complex 15, but does not permit hybridization of capture probe (b) and immobilized probe (a).

In FIG. 2, step (A), an immobilized probe (a) attached to a solid support 10, capture probe (b), and target polynucleotide sequence (c) are labeled as in FIG. 1. A promoter sequence recognized by an RNA polymerase is labeled "P"; "(−)" indicates the 5' end of a nucleic acid and "(+)" indicates the 3' end of a complementary nucleic acid; and a dashed line "(---)" indicates nucleic acid polymerization.

In FIG. 3A, the first hybridization condition allows formation of a capture probe:target polynucleotide:labeled probe complex 30. In FIG. 3B, a second hybridization condition allows formation of an immobilized probe:capture probe:target polynucleotide:labeled probe complex 40, leaving unbound labeled probes 50. In FIG. 3C, the unbound labeled probes have been washed away, leaving the purified immobilized probe:capture probe:target polynucleotide:labeled probe complex 40.

FIG. 5 illustrates a immobilized probe:capture probe:target polynucleotide:primer complex 60 which is a hybridization complex consisting essentially of an immobilized probe oligonucleotide 65 hybridized to a portion of a capture probe oligonucleotide 70 which is hybridized to a portion of a target polynucleotide 75 which is hybridized to a primer oligonucleotide 80. The hybridization complex 60 is attached to a solid support 10 via the immobilized probe 65. The overlapping portions of the lines indicating the oligonucleotides and the target polynucleotide illustrate the portions that hybridize.

FIG. 6, made up of FIGS. 6A to 6E, illustrates an embodiment in which nucleic acid amplification of the captured target nucleic acid 75 is initiated by polymerization from a first primer oligonucleotide 80 which is displaced by subsequent polymerization from a second primer oligonucleotide 90. FIG. 6D illustrates continued synthesis of the complementary strand 85 attached to the first primer oligonucleotide 80 and synthesis of a complementary strand 95 initiating from the second primer oligonucleotide 90. FIG. 6E illustrates continued synthesis of the complementary strand 95 attached to the second primer oligonucleotide 90, displacing the first primer oligonucleotide 80 and its attached complementary strand 85 from the target polynucleotide, making it available to hybridize to a third primer olignucleotide 100 at a position downstream from the first primer oligonucleotide 80.

DETAILED DESCRIPTION OF THE INVENTION

Figure 1A:
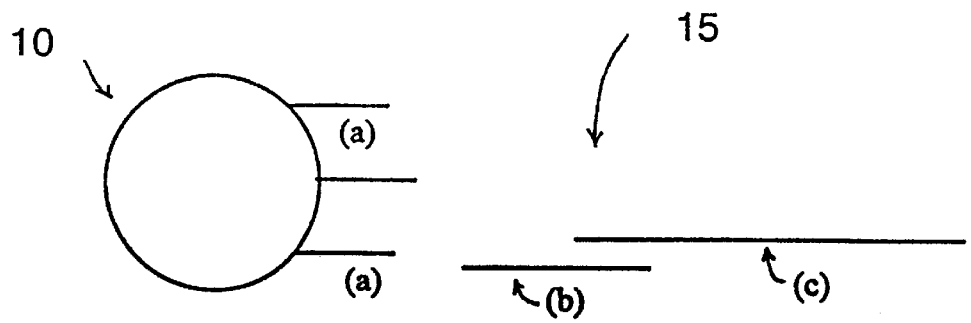
FIGS. 1A and B schematically illustrate the use of two different hybridization conditions to capture a target polynucleotide, labeled "(c)", using an immobilized probe, labeled "(a)", attached to a solid support 10, and a capture probe, labeled "(b)".

The present invention features methods for capturing a target polynucleotide onto a solid support using a capture probe and two different hybridization conditions. Different hybridization conditions are used to control the order of hybridization in a sample containing a target polynucleotide, mixed with a capture probe and an immobilized probe. By a "hybridization condition" is meant the cumulative environment used for a reaction in which one single-stranded nucleic acid hydrogen bonds to a second single-stranded nucleic acid to produce a hybridization complex (which is sometimes referred to herein as a "complex"). The cumulative environment includes, for example, the concentrations and components (e.g., salts, chelating agents and noncompetitive inhibitor nucleic acids) of an aqueous or organic solution containing the single-stranded nucleic acids, and the temperature of the reaction mixture. Other factors that may contribute to the cumulative environment include, for example, the amount of time in which hydrogen bonding is allowed to occur, the physical geometry of the chamber holding the reactants, and the use of mixing or agitation during hybridization. All of these environmental conditions are well known in the art (e.g., See Sambrook et al., *Molecular Cloning, A Laboratory Manual*, 2nd ed. (Cold Spring Harbor Laboratory Press, Cold Spring Harbor, N.Y., 1989)). In the present invention, the first hybridization condition facilitates hybridization of the capture probe to the target polynucleotide while essentially precluding hybridization of the capture probe and the immobilized probe, and a second hybridization condition then facilitates hybridization of the capture probe and the immobilized probe.

An immobilized probe provides means for joining a capture probe to an immobilized support. The immobilized probe is a base sequence recognition molecule joined to a solid support which facilitates separation of bound target polynucleotide from unbound material. Any known solid support may be used, such as matrices and particles free in solution. For example, solid supports may be nitrocellulose, nylon, glass, polyacrylate, mixed polymers, polystyrene, silane polypropylene and, preferably, magnetically attractable particles. Particularly preferred supports are magnetic spheres that are monodisperse (i.e., uniform in size±about 5%), thereby providing consistent results, which is particularly advantageous for use in an automated assay.

The immobilized probe is joined directly, or indirectly, to a solid support by a linkage or interaction which is stable during the first and second hybridization conditions used in the present invention. Direct joining occurs when the immobilized probe molecule is joined to the solid support in the absence of an intermediate group. For example, direct joining may be via a covalent linkage, chelation, or ionic interaction. Indirect joining occurs when the immobilized probe is joined to the solid support by one or more linkers. A "linker" is a means for binding at least two different molecules into a stable complex and contains one or more components of a binding partner set.

Members of a binding partner set are able to recognize and bind to each other. Binding partner sets may be, for example, receptor and ligand, enzyme and substrate, enzyme and cofactor, enzyme and coenzyme, antibody and antigen, sugar and lectin, biotin and streptavidin, ligand and chelating agent, nickel and histidine, substantially complementary nucleotide base recognition molecules, and complementary homopolymeric nucleic acids or homopolymeric portions of polymeric nucleic acids. Components of a binding partner set are the regions of the members that participate in binding.

The methods of the present invention have many different embodiments. In one, a linker is directly joined to the solid support, and is joined to the immobilized probe through components of a binding pair set. In another embodiment, more than one linker is present, where a first linker is directly joined to the solid support and at least one second linker is joined to the immobilized probe through components of a binding pair set. Additional linkers may be used to join the first and second linkers.

A "base sequence recognition molecule" is a polymer containing nucleotide base recognition groups linked together by a backbone. The nucleotide base recognition groups provide sequence information for hybridizing with a complementary molecule. An individual nucleotide base recognition group can hydrogen bond to adenine (A), guanine (G), cytosine (C), thymine (T), uracil (U) or derivatives thereof. The backbone of a base sequence recognition molecule provides the nucleotide base recognition groups with the proper orientation and spacing for hydrogen bonding during hybridization, particularly to bases of a nucleic acid. Base sequence recognition molecules may be, for example, RNA, DNA, peptide nucleic acid, or derivatives thereof.

A capture probe provides means for stably joining a target polynucleotide and an immobilized probe. The capture probe includes one or more base sequence recognition portions: a target polynucleotide-binding region and an immobilized probe-binding region. These two binding regions may be present on one or more base sequence recognition molecules, but preferably are included in a single base sequence recognition molecule containing the two binding regions. In another embodiment, the capture probe includes a target polynucleotide-binding region and an immobilized probe-binding region which are present on two different base sequence recognition molecules joined together by one or more linkers. For example, an immobilized probe-binding region may be present on a first base sequence recognition molecule, the target polynucleotide-binding region may be present on a second base sequence recognition molecule, and the two different molecules are joined by a linker that is a base sequence recognition molecule that hybridizes to the first and second base sequence recognition molecules.

The present invention includes a method of capturing a target polynucleotide present in a sample. First, a mixture including the sample, a capture probe, and an immobilized probe is produced and incubated in a first hybridization condition to form a capture probe:target complex made up of the capture probe hybridized to the target polynucleotide. The first hybridization condition uses a temperature below the $T_m$ of a capture probe:target complex and above the $T_m$ of an immobilized probe:capture probe hybrid. Preferably, in the first hybridization condition, less than at least 50% of the capture probe is in an immobilized probe:capture probe complex. More preferably, in the first hybridization condition, less than 25%, even more preferably, less than 10%, and most preferably less than 1% of the capture probe is in an immobilized probe:capture probe complex.

Then, a second hybridization condition is used to form an immobilized probe:capture probe:target polynucleotide complex made up of the immobilized probe hybridized to the capture probe, which is hybridized to the target polynucleotide. The temperature of the second hybridization condition is below the $T_m$ of the immobilized probe:capture probe hybridization complex, and thus is compatible with the formation of a immobilized probe:capture probe complex. Preferably, the immobilized probe is in excess relative to the capture probe.

"$T_m$" refers to the melting temperature at which 50% of hybridization complexes formed between two base sequence recognition molecules are denatured. At a temperature below the $T_m$, hybridization complex formation is favored, whereas at a temperature above the $T_m$, complex formation is not favored.

Reference to $T_m$ of a hybridization complex containing a capture probe or immobilized probe includes complexes formed via hybridization with one or more linkers which may be present. If linkers are present, then the $T_m$ of a hybridization complex reflects the overall stability of the complex, as can be readily calculated by those skilled in the art. For example, in a capture probe made up of three oligonucleotides there is a first $T_m$ of the first oligonucleotide hybridized to the second oligonucleotide, and a second $T_m$ of the second oligonucleotide hybridized to a third oligonucleotide. The lower of these first and second $T_m$'s determines the stability of the capture probe and whether the three oligonucleotides making up the capture probe remain hybridized at a particular hybridization condition.

The capture probe:target polynucleotide hybridization complex, like other complexes described herein, may contain additional groups besides the indicated components. Such additional groups include, for example, a labeled probe hybridized to the target polynucleotide or an oligonucleotide hybridized to the target which is useful for amplification of the target polynucleotide. Additional groups not affecting the functioning of the present invention may also be present.

A labeled probe is a base sequence recognition molecule containing a detectable group. Detectable groups such as, e.g., a fluorescent moiety, a chemiluminescent moiety, a radioisotope, biotin, avidin, enzyme, enzyme substrate, or reactive group may be included in a labeled probe.

The methods of the present invention may further include a purifying step. By "purifying" is meant that one or more components making up the sample prior to purification are removed from one or more other components of the sample. Sample components include nucleic acids, and may also include materials such as proteins, carbohydrates, lipids and labeled probes. Preferably, the purifying step removes at least about 70%, more preferably at least about 90% and, even more preferably, at least about 95% of the non-target nucleic acid present in the sample.

The methods of the present invention may also include amplifying a purified target polynucleotide following capture (herein referred to as a "captured target") to produce an amplified nucleic acid. Amplifying a target nucleic acid uses a nucleic acid polymerase to produce multiple copies of the entire target polynucleotide or fragments thereof, or of a nucleic acid complementary to the entire target polynucleotide or fragments thereof. Suitable amplification techniques that are well known in the art include, for example, transcription-associated amplification, Polymerase Chain Reaction (PCR), replicase mediated amplification, and Ligase Chain Reaction (LCR).

Amplification of "fragments thereof" refers to production of an amplified nucleic acid containing less than the complete target polynucleotide or the complement thereof. Such fragments may be produced by amplifying a portion of the target polynucleotide, for example, by using an amplification oligonucleotide which hybridizes to, and initiates polymerization from, an internal position of the target polynucleotide. Preferably, the amplified fragment contains a detectable target sequence. The presence of amplified nucleic acid may be detected using different well known techniques, such as, for example, hybridizing a labeled probe to the amplified nucleic acid. Other techniques well known in the art for detecting nucleic acid include, for example, gel filtration, gel electrophoresis, and High Performance Liquid Chromatography (HPLC).

A labeled probe may be used to detect the presence of a purified captured target. Preferably, a purifying step is used to remove unbound labeled probes from bound labeled probes which are hybridized to captured target polynucleotides. The purifying step may be used simultaneously with purifying the captured target polynucleotide. Alternatively, labeled probes may be added to a purified captured target polynucleotide and unbound labeled probes may be removed in a subsequent purifying step.

By "remove" in reference to a sample component or hybridization reaction component, (e.g., unbound labeled probe), is meant that at least 70% of the undesirable component is separated from a retained component. More preferably at least 90% and, even more preferably, at least 95% of the undesirable component is removed. Components may be removed, using standard procedures such as, for example, by using a washing procedure.

The presence of the captured target polynucleotide may be detected using a homogeneous detectable label which may be positioned on the capture probe or on a separate detection probe. A "homogeneous detectable label" refers to a label whose presence can be detected in a homogeneous fashion based upon whether the label is on a molecule hybridized to the target polynucleotide. Thus, the homogeneous detectable label can be detected without physically removing hybridized from unhybridized forms of the label. Homogeneous detectable labels have been previously described, including examples in Arnold et al., U.S. Pat. No. 5,283,174; Woodhead et al., U.S. Pat. No. 5,656,207; and Nelson et al., U.S. Pat. No. 5,658,737.

The immobilized probe may contain one or more repetitious base sequences that are complementary to one or more repetitious base sequences of the capture probe. These complementary repetitious sequences preferably are sequences of at least five bases in length and serve as binding regions (i.e., a capture probe-binding region of the immobilized probe, and an immobilized probe-binding region of the capture probe). The complementary repetitious sequences of the immobilized probe and the capture probe facilitate hybridization between the two probes.

A "repetitious" sequence refers to a sequence of regularly repeating base sequences, such as those formed, for example, by nucleic acid homopolymers of poly-adenine $(A_n)$, poly-thymine $(T_n)$, poly-cytosine $(C_n)$, and poly-guanine $(G_n)$. Repetitious sequences also include those of nucleic acid mixed polymers, such as AT repeats $([AT]_n)$.

Preferably, the repetitious base sequence of the capture probe is longer than a complementary repetitious base sequence of the immobilized probe. The lengths of the complementary repetitious sequences of the two probes determine the $T_m$ of the immobilized probe:capture probe complex. The longer repetitious base sequence of the capture probe facilitates binding to the repetitious base sequence of the immobilized probe because the additional length provides distance between secondary structure of a target polynucleotide that otherwise interferes with hybridization to the immobilized probe.

Preferably, the repetitious base sequence of the immobilized probe is at least about 10 bases, even more preferably about 14 bases in length; and the repetitious base sequence of the complementary capture probe is at least about 10 bases, more preferably is at least about 14 bases, even more preferably is at least about 25 bases in length, and most preferably is about 30 bases in length.

A method of the present invention is used to determine whether a target polynucleotide is present in a sample. The method includes a target capture step that includes two hybridizations, a purifying step, an optional amplifying step and a detecting step. In the presence of a target polynucleotide, in the first hybridization a capture probe-:target polynucleotide complex is produced, and in the second hybridization an immobilized probe hybridizes with the capture probe. Thus, in the presence of a target polynucleotide, the target capture step results in the formation of an immobilized probe:capture probe:target complex comprising an immobilized probe, a capture probe, and a target polynucleotide. If no target polynucleotide is present, then this immobilized probe:capture probe:target complex is not formed and only the immobilized probe:capture probe complex of the second hybridization is formed. The complex formed during the target capture step is purified to produce a purified target polynucleotide for those samples containing the target polynucleotide.

The purified target polynucleotide may be amplified and then detected, or the purified target polynucleotide may be detected without an amplification step. Preferably, the presence of the purified captured target polynucleotide or amplified nucleic acid is detected using a labeled probe. More preferably, the labeled probe hybridizes to the target polynucleotide to form a labeled probe:target polynucleotide complex having a $T_m$ above the temperature of the first hybridization condition. Detection of the labeled probe in the complex indicates the presence of the target polynucleotide in the sample.

When an optional amplification step is included in the method, the purified target polynucleotide is amplified to produce an amplified nucleic acid which is then detected using a labeled probe as described above or by any of a variety of know techniques for detecting nucleic acid (e.g., visualization using a fluorescent intercalating agent). Detection of the amplified nucleic acid indicates that the target polynucleotide was initially present in the sample.

During the hybridization of a capture probe to a target polynucleotide, it is useful to have the capture probe in solution rather than bound to a solid support to maximize the concentration of the free capture probe and to utilize favorable liquid phase hybridization kinetics known to those skilled in the art. That is, solution phase hybridization generally occurs 100-fold faster than a solid phase hybridization that uses the same complementary binding sequences. It is also desirable to add the immobilized probe prior to hybridization of the capture probe to the target polynucleotide to minimize the number of reagent additions and separations, and the complexity of the chemistry. These aspects of the invention are particularly important for an automated assay.

In the methods of the present invention for capturing a target polynucleotide onto a solid support using a capture probe and two different hybridization conditions, the solid support with an immobilized probe, capture probe, and target nucleic acid may be present during both hybridization conditions. The captured target nucleic acid may be purified from other material which is present by washing away the other material using conditions in which the captured target is retained. Then, the purified target polynucleotide may be eluted from the solid support using appropriate conditions, such as by incubating at a temperature above the $T_m$ of the capture probe:immobilized probe complex.

These methods are particularly useful as part of a diagnostic assay in which the target polynucleotide is amplified to produce larger amounts of amplified nucleic acids which are free in solution. The amplified nucleic acids in solution may be detected using well known techniques such as nucleic acid hybridization.

An automated diagnostic assay using the methods of the present invention may be carried out, for example, by: (1) adding a sample suspected of having a target polynucleotide to a container containing a capture probe specific for the target and an immobilized probe which is joined to a solid support; (2) carrying out a two-step hybridization to capture the target polynucleotide onto the solid support by incubating in a first hybridization condition and then lowering the temperature to that of the second hybridization condition; (3) removing sample components not bound to the solid support, for example, by using a washing step; (4) adding to the solid support a solution containing oligonucleotides used in nucleic acid amplification of all or a portion of the target, the appropriate solution components for carrying out amplification, and a probe which hybridizes to amplified nucleic acid and contains a homogeneous detectable label; (5) producing amplified nucleic acid; and (6) detecting the amplified nucleic acid, such as by treating the sample to produce a signal from the label hybridized to the amplified nucleic acid. Detecting the signal indicates the presence of the target polynucleotide in the sample. Different variations of the above scheme may be carried out based on the disclosure provided herein.

Figure 1B:
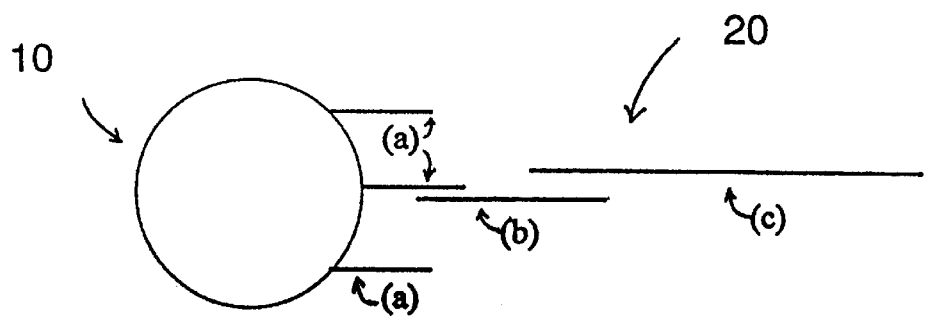
In FIG. 1B, the second hybridization condition permits hybridization of capture probe (b) and immobilized probe (a) to form an immobilized probe:capture probe:target polynucleotide complex 20.
Figure 2:
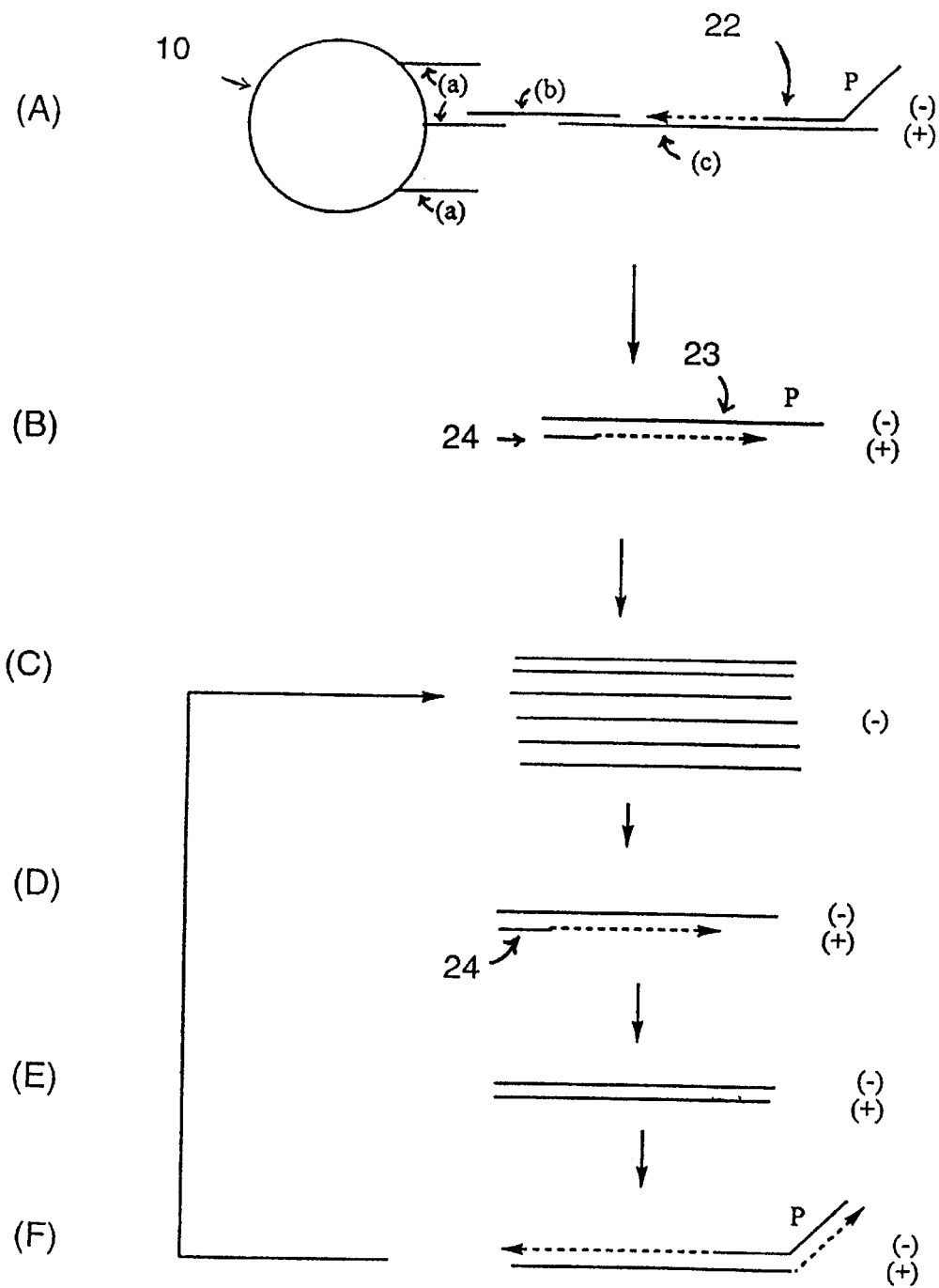
FIG. 2 illustrates steps A through F of a method that includes amplification of a captured target polynucleotide sequence (step (A)) using transcription-associated amplification (steps (B) to (F)).

FIGS. 1 to 3 provide schematic illustrations of the use of the present invention to capture a target polynucleotide, to optionally amplify a polynucleotide target, and to detect the presence of the polynucleotide target. Although FIGS. 1 to 3 illustrate preferred embodiments, those skilled in the art will appreciate that other variations and equivalents can be used to practice the described invention based on the descriptions provided herein. FIG. 4 shows an example of the types of complexes that can be attached to a solid support via an immobilized probe that is a homopolymer.

FIGS. 1A and 1B illustrate the capture of a target polynucleotide. At the beginning of the assay, the immobilized probe (a) is bound to a solid support particle 10, and the capture probe (b) and the target polynucleotide (c) are free in solution. Referring to FIG. 1A, in the first hybridization condition, a capture probe:target polynucleotide complex 15 is formed in solution but the capture probe (b) is substantially unbound to the immobilized probe (a). Then, the reaction in incubated in the second hybridization condition as shown in FIG. 1B. In the second hybridization condition, the capture probe (b) hybridizes to the immobilized probe (a), thereby capturing the target polynucleotide (c) in an immobilized probe:capture probe:target nucleic acid complex 20. Preferably, the second hybridization condition occurs in the same solution by lowering the temperature from that of the first hybridization condition. A specific example of the complexes that can be attached to a solid support via an immobilized probe is illustrated in FIG. 4, described below.

FIG. 2 illustrates one embodiment that further includes amplification of a target polynucleotide sequence (c) using a transcription-associated amplification. The 5' and 3' ends of nucleic acids are indicated by (−) and (+), respectively, on the right-hand side of the figure next to lines representing nucleic acids; using this notation, strands marked "(−)" indicate antisense strands, and strands marked "(+)" indicate sense strands. The dashed line (---) terminating in an arrow (→ or ←) indicates nucleic acid polymerization of a complementary strand of nucleic acid.

In FIG. 2, step (A) illustrates a captured target polynucleotide (c), as described for FIG. 1B, that has been hybridized to an oligonucleotide containing a promoter sequence "P" to form a nucleic acid hybridization complex 22. Using a polymerase such as a reverse transcriptase, a complementary DNA is synthesized (shown by ---). In step (B), (−) strand is hybridized to a primer 24 and reverse transcriptase is used to form a DNA duplex 23 containing a double-stranded promoter P by polymerization (shown by ---). In step (B), the complex 23 is shown free in solution, although it need not be released from the solid support 10. Making the (−) strand available for hybridization with a primer 24 may be achieved using different techniques well known in the art, such as, by using a denaturing step, or RNase H activity. Preferably, RNase H activity is used when the target is an RNA.

FIG. 2, steps (C) to (E) illustrate production of amplified nucleic acid from the product of step (B). An RNA polymerase, such as T7 RNA polymerase, is used to generate multiple sense RNA transcripts (step (C)) to which the primer 24 can bind (step (D)) for primer extension. The dashed line in step (D) illustrates primer extension. The primer 24, sometimes referred to as a promoter primer, may be added prior to commencing amplification.

Between steps (C) to (F), the (−) strands are made available for hybridization to a promoter-primer 24. FIG. 2, steps (D) to (F) illustrate the use of a promoter-primer to form a double-stranded promoter which is recognized by an RNA polymerase and used to produce additional RNA transcripts. The produced transcripts may be used in another cycle of amplification (indicated by the arrow at the left of FIG. 2 connecting steps (F) and (C)). The steps of amplification are described in greater detail below under "Transcription-Associated Amplification."

Figure 3A:
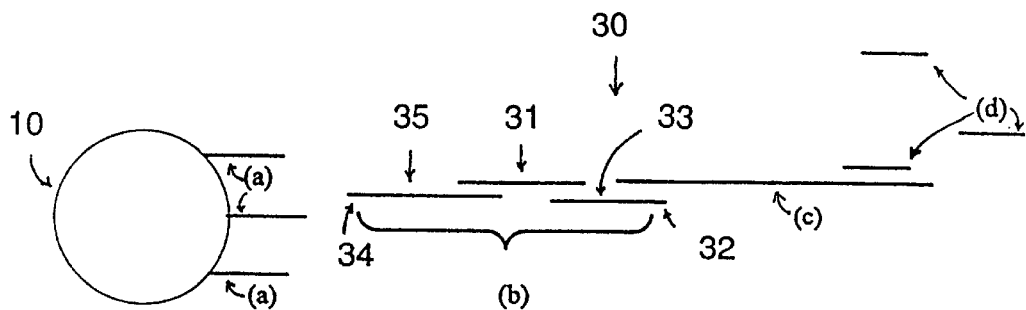
FIGS. 3A, 3B and 3C illustrate the use of two different hybridization conditions to detect the presence of a target polynucleotide (c), using an immobilized probe (a), attached to solid support 10, a capture probe (b), labeled as in FIG. 1, and labeled probes shown as "(d)".
Figure 3B:
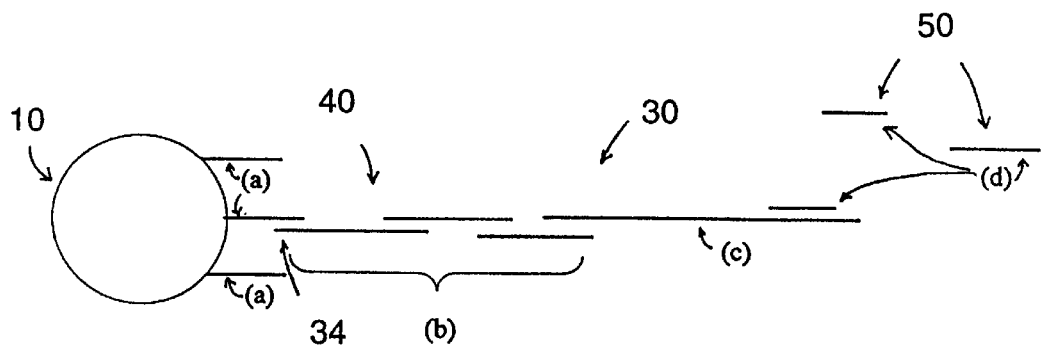
Figure 3C:
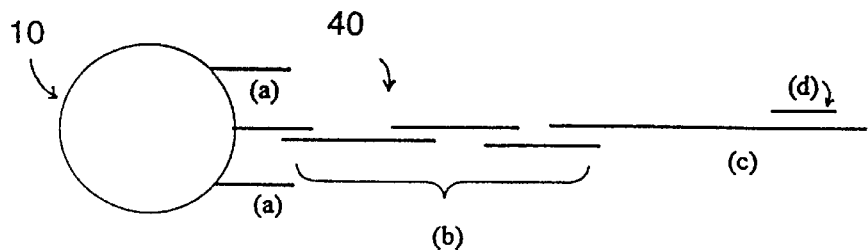
Figure 4:
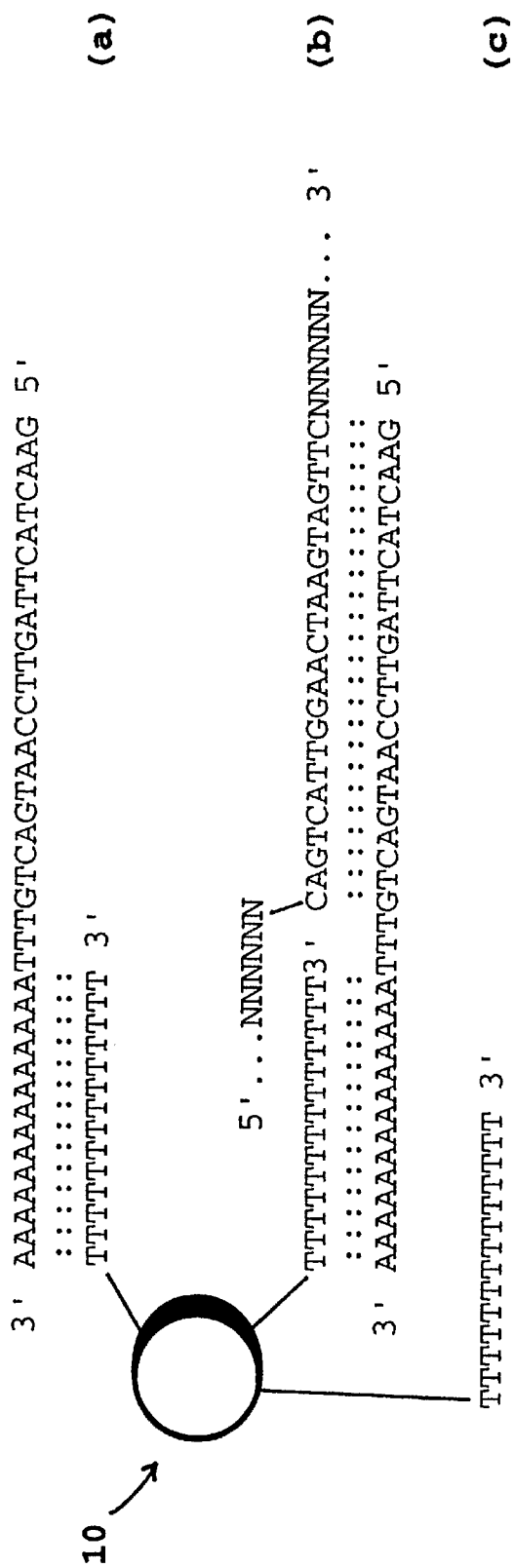
FIG. 4 illustrates an example of a solid support 10 with attached immobilized probes consisting of $T_{14}$ sequences; the upper probe (adjacent to "(a)" at the right side) is in immobilized probe:capture probe complex in which the $T_{14}$ immobilized probe is hybridized (shown as ":" between bases) to a capture probe (3' $A_{14}$TTTGTCAGTAACCTTGATTCATCAAG 5' (SEQ ID NO:1)) containing a complementary $A_{14}$ sequence; the middle probe (adjacent to "(b)" at the right side) is in an immobilized probe:capture probe:target polynucleotide complex which contains the immobilized probe hybridized to the capture probe which is hybridized to a target sequence (5' CAGTCATTGGAACTAAGTAGTTC 3' (SEQ ID NO:2)) within a larger sequence (indicated by terminal "NNNNNN" sequences); and the lower probe (adjacent to "(c)" at the right side) is an unhybridized immobilized $T_{14}$ probe.

FIGS. 3A through 3C illustrate the capture and detection of a target polynucleotide (c) with a labeled probe (d). At the beginning of the assay, the reagent mixture includes the immobilized probe (a) bound to a solid particle 10, the capture probe (b), the target polynucleotide (c), and the labeled probe (d) free in solution. As shown in FIG. 3A, in the first hybridization condition, a capture probe:target polynucleotide:labeled probe hybridization complex 30 is formed in solution. The capture probe (b) of FIG. 3A consists of a linker 31 joining a first base sequence recognition polynucleotide 33 and a second base sequence recognition polynucleotide 35. The first base sequence recognition polynucleotide 33 includes a target polynucleotide-binding region 32, and the second base sequence recognition polynucleotide 35 includes an immobilized probe-binding region 34.

As shown in FIG. 3B, in the second hybridization condition the capture probe:target polynucleotide:labeled probe hybridization complex 30 hybridizes to the immobilized probe (a), thereby producing an immobilized probe:capture probe:target polynucleotide:labeled probe complex 40 (i.e., a bound labeled probe). This complex 40 is formed when the immobilized probe (a) hybridizes with the immobilized probe-binding region 34. The second hybridization condition may be achieved by lowering the temperature of the first hybridization condition.

Referring to FIG. 3C, a washing step may be used to remove unbound labeled probe (not shown) from the bound labeled probe (d) present in the complex 40 attached to the solid support 10. Detection of the bound labeled probe (d) is an indication of the initial presence of the target polynucleotide in the sample.

FIG. 4 illustrates an example of a solid support 10 to which are attached immobilized probes shown as $T_{14}$ sequences. The upper immobilized probe (marked (a) at the right) is shown in an immobilized probe:capture probe complex in which the $T_{14}$ probe is hybridized (shown as ":" between bases) to a complementary $A_{14}$ sequence of a capture probe shown as 3' $A_{14}$TTTGTCAGTAACCTTGATTCATCAAG 5' (SEQ ID NO:1). The middle immobilized probe (marked (b) at the right) is shown in an immobilized probe:capture probe:target polynucleotide complex which contains the components of the immobilized probe:capture probe complex with the 5' region of the capture probe hybridized to a complementary target sequence shown as 5' CAGTCATTGGAACTAAG-TAGTTC 3' (SEQ ID NO:2). The target sequence illustrated is an internal sequence as indicated by terminal "NNNNNN" sequences. The lowest immobilized probe (marked (c) at the right) is unhybridized.

In one embodiment, the immobilized hybridization complex that contains the target polynucleotide further includes a primer oligonucleotide that is used to initiate polymerization synthesis in a nucleic acid amplification reaction catalyzed by a DNA polymerase activity (e.g., provided by a reverse transcriptase or DNA polymerase enzyme). FIG. 5 illustrates such an immobilized hybridization complex 60. The immobilized probe:capture probe:target polynucleotide:primer complex 60 consists essentially of an immobilized probe 65 which is hybridized to a portion of a capture probe 70 which is hybridized to a portion of a target polynucleotide 75 which is hybridized to a primer 80. The hybridization complex is immobilized because it is attached to a solid support 10 via the immobilized probe 65. This hybridization complex can form during the hybridization conditions that are used to capture the target polynucleotide, thus allowing amplification to initiate without first providing an incubation step to hybridize the primer oligonucleotide to the target polynucleotide in an amplification reaction mixture. Because the primer hybridized to the target polynucleotide during the capture step is present in the amplification mixture at the beginning of the reaction (i.e., when amplification reaction reagents are added) it can initiate cDNA synthesis from the template polynucleotide without a separate step to anneal the primer to the template strand. This makes the amplification reaction more efficient than one which typically requires an initial primer hybridization incubation, usually at elevated temperature and in a hybridization solution, followed by cooling the mixture, diluting the hybridization solution and adding additional reagents needed for amplification, and adding enzyme(s) needed to synthesize the amplified nucleic acid. In addition to eliminating a separate primer annealing step, the presence of the primer oligomer already hybridized to the target polynucleotide simplifies adding the amplification reagents (e.g., salts, buffers, NTP and enzyme(s)) because they can be added substantially simultaneously, without the potential for heat inactivating enzyme(s) during a primer annealing step at elevated temperature (e.g., 60° C.). Further adding to the efficiency of amplification, the immobilized probe:capture probe:target polynucleotide:primer complex can be washed to remove components that might interfere with the amplification reaction and then the immobilized complex can be added directly to an amplification reaction mixture where the hybridized primer is used to initiate synthesis of a complementary strand, e.g., a cDNA version of the target. Because some of the primer oligonucleotide present in the hybridization reaction may be washed away in the process of washing the immobilized probe:capture probe:target polynucleotide:primer complex (e.g., because hybridization was not 100% efficient), additional primer that is substantially identical to the primer present in the immobilized complex is present in the amplification reaction mixture to ensure sufficient primer oligonucleotide for subsequent polymerization steps.

Hybridization of the primer oligonucleotide to the target polynucleotide during the target capture step can occur when the primer is added to the mixture of the sample containing the target polynucleotide, the capture probe and the immobilized probe. Then, depending on the $T_m$ of the primer:target polynucleotide hybridization complex, the primer hybridizes to the target polynucleotide in the first or second hybridization condition. Whether hybridization of the primer oligonucleotide occurs during the first or second hybridization incubation step, both result in formation of a target polynucleotide:primer oligonucleotide complex that is captured to the solid support via the interaction of the capture probe and the immobilized probe. In one embodiment, the primer hybridizes to the target polynucleotide in solution in the first hybridization condition in which the capture probe:target polynucleotide complex is formed, thus producing in solution a hybridization complex consisting essentially of capture probe, target polynucleotide and primer oligonucleotide, while the capture probe is substantially unbound to the immobilized probe. Incubation in the second hybridization condition, in which the capture probe and the immobilized probe hybridize, then results in capture of the complex that includes the primer. The complex is made up essentially of immobilized probe, capture probe, target polynucleotide and primer oligonucleotide (i.e., an immobilized probe:capture probe:target polynucleotide:primer complex). In another embodiment, the primer hybridizes to the target polynucleotide during the second hybridization condition, after the capture probe and target polynucleotide have hybridized and while the immobilized probe and capture probe hybridize to capture the complex that includes the target polynucleotide. In this embodiment also, the captured complex is the immobilized probe:capture probe:target polynucleotide:primer complex. It will be appreciated that, to avoid competition for hybridization to the same or overlapping sequences, the portion of the target polynucleotide that hybridizes specifically to the target-binding portion of the capture probe is different from and does not overlap with the portion of the target polynucleotide that hybridizes specifically with the primer oligonucleotide.

When the immobilized probe:capture probe:target polynucleotide:primer oligonucleotide complex has been formed and isolated from other sample components, the captured target polynucleotide and primer may be separated from the complex for use in a nucleic acid amplification reaction. For example, by heating the immobilized complex above the $T_m$ of the immobilized probe:capture probe hybridization complex, the immobilized probe and capture probe separate, releasing the capture probe, target polynucleotide, and primer oligonucleotides from the solid support. Depending on the temperature used to release the capture probe from the immobilized probe, the capture probe:target polynucleotide:primer oligonucleotide complex may remain hybridized or may be melted apart into the individual components. Generally, to avoid a hybridization step that reforms the target polynucleotiude:primer oligonucleotide complex for nucleic acid synthesis initiating from the 3' end of the primer oligonucleotide and using the target polynucleotide as a template, it is preferable to maintain the target polynucleotide:primer oligonucleotide hybridization complex formed during the target capture step for use in a subsequent amplification step. In one embodiment, the immobilized probe:capture probe:target polynucleotide:primer oligonucleotide complex is maintained intact and the entire complex is put into an amplification reaction mixture where nucleic acid synthesis to amplify the target sequence takes place.

Figure 6A:
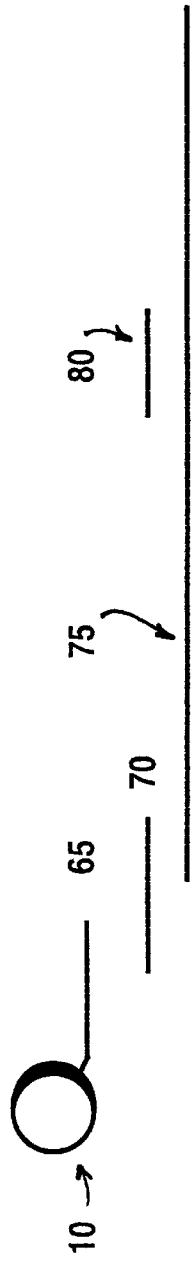
FIG. 6A illustrates an immobilized probe-:capture probe:target polynucleotide:primer complex substantially as shown in FIG. 5 in which a hybridization complex consisting essentially of an immobilized probe oligonucleotide 65 (attached to a solid support 10) and hybridized to a portion of a capture probe oligonucleotide 70 which is hybridized to a portion of a target polynucleotide 75 which is hybridized to a first primer oligonucleotide 80.
Figure 6B:
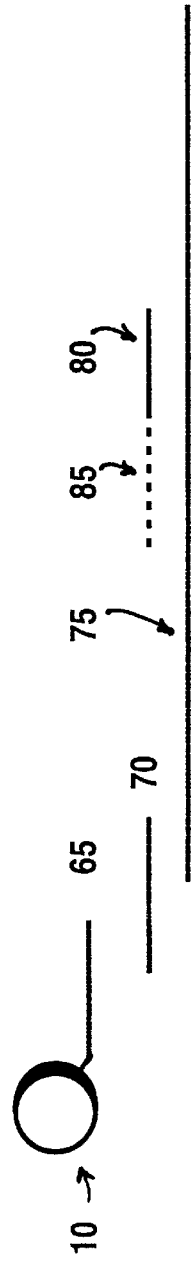
FIG. 6B shows the hybridization complex of FIG. 6A in which nucleic acid synthesis produces a complementary strand 85 to the target polynucleotide 75 by initiating polymerization from the first primer oligonucleotide 80.
Figure 6C:
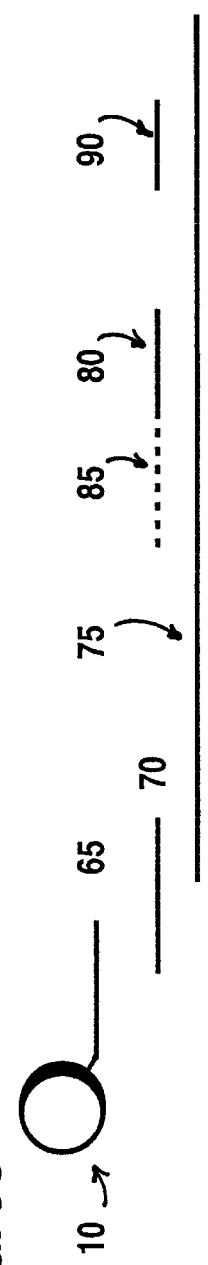
FIG. 6C illustrates a step in which a second primer oligonucleotide 90 has hybridized to the target polynucleotide 75 upstream of the first primer oligonucleotide 80.

In one embodiment, illustrated by FIGS. 6A to 6E, nucleic acid amplification of the captured target nucleic acid 75 is initiated by polymerization from a first primer oligonucleotide 80 which is hybridized to the target polynucleotide during target capture as described above. In this embodiment, a second primer oligonucleotide 90 is hybridized upstream from the first primer oligonucleotide and used to displace the first primer oligonucleotide and its attached polymerized nucleic acid strand that is formed during the initial strand polymerization step from the template target polynucleotide. FIG. 6A illustrates an immobilized probe:capture probe:target polynucleotide:primer complex substantially as shown in FIG. 5 and formed as described above. This hybridization complex consists essentially of an immobilized probe oligonucleotide 65 (attached to a solid support 10) which is hybridized to a portion of a capture probe oligonucleotide 70 which is hybridized to a portion of a target polynucleotide 75 which is hybridized to a first primer oligonucleotide 80. Upon addition of amplification reagents and enzyme(s) the hybridization complex of FIG. 6A, nucleic acid synthesis initiates to produce a complementary strand 85 to the target polynucleotide 75 by polymerization that starts from the 3' end of the first primer oligonucleotide 80. In the amplification reaction mixture, a second primer oligonucleotide 90 is present and hybridizes to the target polynucleotide 75 upstream of the first primer oligonucleotide 80 as shown in FIG. 6C. As amplification mediated by a DNA polymerase activity proceeds, as shown in FIG. 6D, synthesis of the complementary strand 85 attached to the first primer oligonucleotide 80 continues and synthesis of a complementary strand 95 initiates from the 3' end of the second primer oligonucleotide 90. FIG. 6E illustrates continued synthesis of the complementary strand 95 attached to the second primer oligonucleotide 90, producing a complementary strand that displaces the first primer oligonucleotide 80 and its attached complementary strand 85 from the target polynucleotide. The displaced complementary strand attached to the first primer oligonucleotide thus becomes available for hybridization with third primer olignucleotide 100 at a position downstream from the first primer oligonucleotide 80. The complementary nucleic acid with the first primer end and the hybridized third primer oligonucleotide then is further amplified during the nucleic acid amplification reaction by polymerization of a strand that initiates from the 3' end of the third primer oligonucleotide, using the complementary strand initiated from the first primer as its template. If the first primer oligonucleotide is a promoter primer (e.g., a primer that has a 5' promoter sequence), then polymerization from the third primer will make a double-stranded functional promoter sequence that can be recognized by the RNA polymerase specific for the promoter sequence. In the presence of appropriate substrates, transcription of multiple RNA transcripts made from the double-stranded DNA sequence will produce amplified copies of a portion of the target polynucleotide that was initially captured in the immobilized probe:capture probe:target polynucleotide:primer complex. If additional first primer oligonucleotides or functionally equivalent oligonucleotides are present in the amplification reaction mixture, the RNA transcripts can hybridize to the oligonucleotides and a cDNA strand is polymerized mediated by the DNA polymerase activity of the reverse transcriptase in the reaction mixture.

The cDNA, in turn, is available to hybridize to the third primer oligonucleotide and polymerization from the third primer makes a double-stranded functional promoter sequence recognized by the RNA polymerase to continue the cycle of producing multiple transcripts to amplify the target sequence present in the target polynucleotide.

Base Sequence Recognition Molecules

Base sequence recognition molecules contain sequence information that permits hybridization to sufficiently complementary nucleic acids in appropriate reaction conditions. By "sufficiently complementary" is meant a contiguous nucleic acid base sequence that is capable of hybridizing to a base sequence recognition molecule (e.g., another contiguous nucleic acid base sequence) by hydrogen bonding between complementary bases. The complementary base sequence may be complementary at each position in the base sequence recognition molecule using standard base pairing (e.g., G:C, A:T or A:U pairing). Alternatively, the complementary base sequence may contain one or more residues that are not complementary using standard hydrogen bonding (including a basic "nucleotides"), but the entire complementary base sequence is capable of specifically hybridizing with the base sequence recognition molecule in appropriate hybridization condition. Appropriate hybridization conditions are well known to those skilled in the art, can be predicted readily based on sequence composition, or can be determined empirically by using routine testing (e.g., See Sambrook et al., *Molecular Cloning, A Laboratory Manual*, 2nd ed. (Cold Spring Harbor Laboratory Press, Cold Spring Harbor, N.Y., 1989) at §§ 1.90–1.91, 7.37–7.57, 9.47–9.51 and 11.47–11.57 particularly at §§ 9.50–9.51, 11.12–11.13, 11.45–11.47 and 11.55–11.57). These base sequence recognition molecules may contain additional groups not providing sequence information. The additional groups, if present, do not prevent hybridization of a base sequence recognition molecule to a sufficiently complementary nucleic acid in the reaction conditions.

A base sequence recognition molecule comprises nucleotide base recognition groups joined together by a backbone. The nucleotide base recognition groups can hydrogen bond with nucleotide nitrogenous bases present in a nucleic acid. The backbone provides a proper conformation and spacing to allow the groups to hydrogen bond to nucleotides of a nucleic acid.

A given nucleotide base recognition group may be complementary to a particular nucleotide (e.g., A, G, C, T, and U), and thus, be able to hydrogen bond with that nucleotide present in a nucleic acid. A nucleotide base recognition group may also be able to hydrogen bond with different bases (e.g., a nucleotide base recognition group of inosine (I) can hydrogen bond with U, A, or C).

Preferred nucleotide base recognition groups are nitrogenous purine or pyrimidine bases, or derivatives thereof, which are able to hydrogen bond with either A, G, C, T, U or I. Examples of base recognition groups include A, G, C, T, U, or I, and derivatives thereof. Examples of derivatives include modified purine or pyrimidine bases such as $N^4$-methyl deoxygaunosine, deaza- or aza-purines and deaza- or aza-pyrimidines used in place of natural purine and pyrimidine bases, pyrimidine bases having substituent groups at the 5 or 6 position, and purine bases having an altered or a replacement substituent at the 2, 6 or 8 positions. Such derivative and their synthesis are well known in the art (see, Cook, PCT Int'l Pub. No. WO 93/13121). Additional examples are 2-amino-6-methylaminopurine, $O^6$-methylguanine, 4-thio-pyrimidines, 4-amino-pyrimidines, 4-dimethylhydrazine-pyrimidines, $O^4$-alkyl-pyrimidines, and others known in the art.

The backbone of a base sequence recognition molecule may be made up of different groups or linkages known in the art. Preferably, the backbone contains one or more of: sugar-phosphodiester linkages, peptide nucleic acid backbone groups, phosphorothioate linkages, or combinations thereof.

Structure I illustrates a sugar-phosphodiester type backbone group where the sugar group is a pentofuranosyl group. The sugar groups are joined together by a phosphodiester linkage or other suitable linkage.

STRUCTURE I

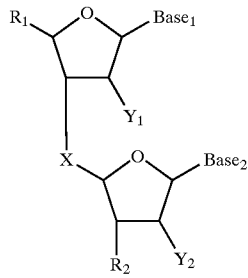

Referring to Structure I, X represents the group joining two sugars. Examples of X include, —P(O)$_3$—, —NHP(O)$_3$—, —OCOO—, OCH$_2$CONH—, —OCH$_2$COO— and —OCONH—. As with the other examples provided herein, based on the disclosure provided, other equivalents well known in the art may also be used. $Y_1$ and $Y_2$ are independently selected groups. Examples of $Y_1$ and $Y_2$ include H, OH, an alkoxy containing up to 4 carbon atoms, halogen, and $C_1$–$C_4$ alkyl. Preferably, $Y_1$ and $Y_2$ are independently either H, OH, F, or OCH$_3$. Base$_1$ and Base$_2$ are independently selected nucleotide base recognition groups. Preferably, Base$_1$ and Base$_2$ are independently either A, G, C, T, U or I. $R_1$ and $R_2$ represent independently selected groups which may include additional sugar-phosphodiester type groups, peptide nucleic acid, and moieties not providing sequence information such as abasic "nucleotides" (containing a phosphodiester backbone, but lacking a nucleotide base recognition group), polymers such as polyethylene glycol, polysaccharides, polypeptides, peptides, and other well-known non-nucleotide linkages (see Arnold et al., U.S. Pat. No. 5,585,481).

Derivatives of Structure I that may be a component of a base sequence recognition molecule are known in the art such as molecules having a different type of sugar in the backbone. For example, a base sequence recognition molecule may have cyclobutyl moieties connected by linking moieties, where the cyclobutyl moieties have heterocyclic bases attached thereto (e.g., see Cook et al., PCT Int'l Pub. No. WO 94/19023).

Another type of backbone of a base sequence recognition molecule is a peptide-type bond, such as that present in peptide nucleic acid. "Peptide nucleic acid" refers to a DNA analogue where the deoxyribose phosphate backbone is replaced by a pseudopeptide backbone as described previously (Hyrup & Nielsen, 1996, *Bioorg. & Med. Chem.* 4:5–23; Hydig-Hielsen et al., PCT Int'l Pub. No. WO 95/32305). Preferably, the peptide nucleic acid is made up of N-(2-aminoethyl)glycine units as illustrated in Structure II, in which $R_1$, $R_2$, and Base$_1$ are as described for Structure I.

STRUCTURE II

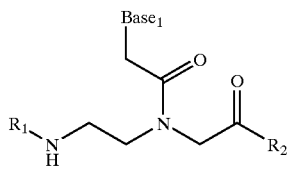

Base sequence recognition molecules can be produced using known methods, such as standard organic synthesis methods for producing oligonucleotides and modified oligonucleotides (for example, see Eckstein, F., *Oligonucleotides and Analogues, a Practical Approach*, chapters 1–5, 1991; Caruthers et al., *Meth. In Enzymol.*, vol. 154, p. 287, 1987; Bhatt, U.S. Pat. No. 5,252,723; Klem et al., PCT Int'l Pub. No. WO 92/07864; Cook, PCT Int'l Pub. No. WO 93/13121; Miller et al., PCT Int'l Pub. No. WO 94/15619; McGee et al., PCT Int'l Pub. No. WO 94/02051; Cook et al., PCT Int'l Pub. No. WO 94/19023; Hyrup et al., *Bioorg. Med. Chem.* 4:5–23, 1996; and Hydig-Hielsen et al., PCT Int'l Pub. No. WO 95/32305; Ordoukhanian et al., *Nuc. Acids Res.* 25(19):3783–3786, 1997; Myer et al., *Bioconjug. Chem.* 7(4):401–412,1996; Schultz et al., *Nuc. Acids Res.* 24(15):2966–2973, 1996; Woo et al., *Nuc. Acids Res.* 24(13):2470–2475, 1996; Agris et al., *Biochimie* 77:125–134, 1995; Berressem et al., *Nuc. Acids Res.* 23(17):3465–3472, 1995; Seela et al., *Nuc. Acids Res.* 23(13):2499–2505, 1995; Vinayak et al., *Nuc. Acids Symp. Ser.* 33:123–125, 1995; Limbach et al., *Nuc. Acids Res.* 22(12):2183–2196, 1994; Gryaznov et al., *Nuc. Acids Res.* 20(8):1879–1882,1992; Kawana et al., *Nuc. Acids Symp. Ser.* 25:93–94, 1991; Pfleiderer et al., *Nuc. Acids Symp. Ser.* 24:29–32, 1991; Wagner et al., *Nuc. Acids Res.* 19(21):5965–5971, 1991; Marquez et al., *Nuc. Acids Symp. Ser.* 22:35–36, 1990; Lin et al., *Nuc. Acids Res.* 17(24):10373–10383, 1989; Farrance et al., *Anal. Biochem.* 179(1):60–65, 1989; Gildea et al., *Nuc. Acids Res.* 17(6):2261–2281, 1989; Yeung et al., *Nuc. Acids Res.* 16(10):4539–4554, 1988; Pon et al., *Nuc. Acids Res.* 13(18):6447–6465, 1985; Millican et al., *Nuc. Acids Res.* 12(19):7435–7453, 1984; Schinazi et al., *J. Med. Chem.* 21(11):1141–1146,1978).

Preferred base sequence recognition molecules independently include: (i) a backbone including at least one sugar-phosphodiester type group, at least one peptide nucleic acid group, at least one phosphorothioate group, or a combination thereof, and (ii) independently selected nucleotide base recognition groups able to hydrogen bond to A, G, C, T, U or I, joined to the backbone. Base sequence recognition molecules may include components which are deoxynucleotides, ribonucleotides, 2'-methoxy substituted ribonucleotides, or 2'-halo substituted ribonucleotides. Preferably, one or more of the referenced components make up at least about 70%, more preferably at least about 80%, still more preferably at least about 90%, and most preferably about 100% of the base sequence recognition molecule.

Immobilization to a Solid Support

A base sequence recognition molecule may be joined by various known means to different types of supports to form an immobilized probe. Covalent attachment of oligonucleotides synthesized using standard chemical techniques to a solid support has been described previously (Lund, et al., *Nuc. Acids Res.*16:10861–10880, 1988; European Pat. App. Pub. No. 0444120). Particularly preferred solid supports are magnetically attractable particles which are useful in a separation step because the particles can be attracted to a reaction container location and held in place while unbound solution components are washed away. Magnetically attractable particles can be produced using standard techniques or obtained from readily available commercial sources.

$T_m$ and Hybridization Conditions

The methods of the present invention vary the hybridization conditions to control the timing of the formation of a capture probe:target complex and an immobilized probe::capture probe complex. As discussed in more detail above, the primer oligonucleotide can hybridize to the target polynucleotide during either of the hybridization conditions to form an immobilized probe:capture probe:target polynucleotide:primer complex. The ability of two base sequence recognition molecules to hybridize depends upon the structures and the surrounding reaction environment. The reaction environment includes the composition of the solution containing two or more recognition molecules and the solution temperature.

Using a particular assay composition, a hybridization complex is not stable when the assay temperature is above the $T_m$ of the complex. Solution factors well known in the art, such as salt concentration and the presence of denaturing agents, can affect the $T_m$ of a given complex. Two base sequence recognition molecules making up a hybridization complex can be constructed to have $T_m$ characteristics suitable for use in the present invention based on descriptions provided herein and techniques well known in the art (e.g., see Sambrook et al., *Molecular Cloning, A Laboratory Manual*, $2^{nd}$ ed. (Cold Spring Harbor Laboratory Press, Cold Spring Harbor, N.Y., 1989) at §§ 1.90–1.91, 7.37–7.57, 9.47–9.51 and 11.47–11.57, particularly §§ 9.50–9.51, 11.12–11.13, 11.45–11.47, 11.55–11.57).

Hybridization complex stability is affected by the length and the degree of complementarity between two base sequence recognition molecules, the nucleotide base recognition groups, and the backbone of the base sequence recognition molecule. For example, the $T_m$ of a complex formed between two base sequence recognition molecules can be lowered by constructing the molecules to have internal regions of less than 100% complementarity to each other. This may be achieved by including mismatches or linker components such as non-nucleotide linkers and abasic "nucleotides." Linker components may be positioned opposite a base in an opposing strand or can "bulge" out of a strand, thereby decreasing complex stability. The type of nucleotide base recognition groups which are present on opposing strands will also affect stability of a probe hybridization complex. For example, G:C pairing is stronger than A:T pairing, due to more hydrogen bonds in G:C pairs.

The backbone composition of a base sequence recognition molecule may be adjusted in different ways to affect hybridization complex stability. Preferred backbones are peptide linkages such as those present in peptide nucleic acid, and sugar-phosphodiester type linkages such as those present in ribonucleic acids and deoxyribonucleic acids, or derivatives thereof. Peptide nucleic acids generally form a more stable complex with RNA than with the corresponding DNA sequence. More preferably, the backbone is made up of sugar-phosphodiester type linkages in which both the sugar group and the linkage joining the group can affect complex stability. For example, the sugar effect can be demonstrated with 2'-methoxy substituted RNA groups, in which a hybridization complex formed between 2'-methoxy substituted RNA and the complementary 2' OH RNA is generally more stable than a corresponding DNA:RNA complex. A 2'-fluoro substituted RNA has essentially the same type of effect as 2'-methoxy substituted RNA on complex stability. For this reason, an initiating primer that binds to an RNA target polynucleotide often contains one or more 2'-O-methoxy linkages.

A linkage joining two sugar groups may affect hybridization complex stability by affecting the overall charge or the charge density, or by affecting steric association between two molecular components. Steric interactions from bulky linkages produce "bulges" that reduce complex stability. Linkages with charged (e.g., phosphorothioates) or neutral (e.g., methylphosphonates) groups can affect complex stability.

$T_m$ can be predicted using standard calculations and measured using routine testing techniques well known in the art. Such methods are described, for example, in Sambrook et al., *Molecular Cloning, A Laboratory Manual*, $2^{nd}$ ed. (Cold Spring Harbor Laboratory Press, Cold Spring Harbor, N.Y., 1989) at §§ 1.90–1.91, 7.37–7.57, 9.47–9.51 and 11.47–11.57, particularly at §§ 9.50–9.51, 11.12–11.13, 11.45–11.47 and 11.55–11.57), and Hogan et al., U.S. Pat. No. 5,547,842.

In the first hybridization solution of preferred embodiments of the present invention, the $T_m$ of the capture probe:target polynucleotide complex is greater than the $T_m$ of the immobilized probe:capture probe complex by at least about 5° C., preferably by at least about 10° C., more preferably by at least about 20° C., and most preferable by at least about 25° C. Similarly, when hybridization of the primer oligonucleotide to the target polynucleotide occurs in the same hybridization condition in which the capture probe hybridizes to the target polynucleotide, the $T_m$ of the primer:target polynucleotide complex is greater than the $T_m$ of the immobilized probe:capture probe complex by at least about 5° C., preferably by at least about 10° C., more preferably by at least about 20° C., and most preferable by at least about 25° C.

Changing the Hybridization Conditions

The preferred method of changing the hybridization conditions is by changing the temperature of the hybridization solution containing assay components. Changes in temperature may readily be achieved without adding reagents to the solution and, thus, are more compatible with automation. An automated assay is a preferred embodiment of the present invention. Preferably, the second hybridization condition is achieved by lowering the temperature of the first hybridization condition by at least about 10° C., more preferably by at least about 15° C., still more preferably by at least about 20° C., and most preferably by at least about 25° C. However, any known method of lowering the stringency of a hybridization condition, such as by increasing the ionic strength of the solution or diluting the solution with denaturants, may be used to achieve the second hybridization condition.

Amplification

Amplification is used to increase the number of copies of the target polynucleotide. Amplification conditions are compatible with nucleic acid polymerization to produce a nucleic acid strand complementary to a nucleic acid template by using at least one nucleic acid polymerase. Amplification conditions include one or more enzymes, amplification oligonucleotides, nucleoside triphosphate substrates, buffer conditions, and incubation at an appropriate temperature. The specific conditions are well known in art and depend upon the type of nucleic acid amplification used.

Enzymes.

Suitable nucleic acid polymerases for carrying out nucleic acid amplification procedures are readily available commercially or can be isolated and purified. Such polymerases include, for example, DNA-dependent DNA polymerases such as DNA polymerase I isolated from *Escherichia coli*, *Bacillus stearothermophilus* or *B. caldotenex*, T4 DNA polymerase, and Taq polymerase. Other suitable enzymes are DNA-dependent RNA polymerases such as, for example, T7 RNA polymerase, T3 RNA polymerase, and SP6 RNA polymerase. Suitable enzymes also include RNA-dependent DNA polymerases such as, for example, avian myeloblastosis virus (AMV) reverse transcriptase and Moloney murine leukemia virus (MMLV) reverse transcriptase. Amplification may also be accomplished using replicases (e.g., Qβ-replicase), ligases (e.g., *E. coli* DNA ligase and T4 DNA ligase) or combinations of enzymes.

For the examples presented herein, the units of enzyme activity are defined as follows. For Moloney murine leukemia virus reverse transcriptase (MMLV RT), 1 unit of MMLV-RT incorporates 1 nmol of dTTP in 10 min at 37° C. using 200–400 µmolar oligo dT-primed poly(A) as template. For T7 RNA polymerase (T7 RNAP), 1 unit of T7 RNAP incorporates 1 nmol of ATP into RNA in 1 hr at 37° C. using a DNA template containing a T7 promoter.

Amplification Oligonucleotides

"Amplification oligonucleotides" are oligonucleotides which hybridize to a target nucleic acid, or its complement, and participate in an amplification reaction. Examples of amplification oligonucleotides include primers and promoter-primers.

The selection of amplification oligonucleotides depends upon the amplification method used and the nucleic acid being amplified. A particular amplification oligonucleotide may be readily designed and synthesized by one skilled in the art depending on the sequence of the desired target nucleic acid and the amplification method chosen by the practitioner of the present invention. Examples of commonly used amplification oligonucleotides include those which are analogous or complementary to a nucleotide base sequence and which may optionally contain nucleic acid sequence regions that are not complementary to the target nucleic acid. For example, an amplification oligonucleotide may contain a promoter sequence recognized by an RNA polymerase, or a base sequence recognized by a replicase.

An analogous amplification oligonucleotide includes a region capable of hybridizing to a nucleic acid that is perfectly complementary to a region of the target nucleic acid (e.g., a cDNA when the target nucleic acid is an RNA). The analogous oligonucleotide may hybridize to the complementary nucleic acid at a position located near the 3' end of the complementary target sequence. The analogous oligonucleotide may also contain a non-complementary region, such as a promoter sequence region, and/or one or more modifications, such as a modification that inhibits nucleic acid polymerase activity. Preferably, the analogous oligonucleotide contains at least about 10 contiguous bases, and more preferably at least about 12 contiguous bases, which are complementary to the nucleic acid that is perfectly complementary to a region of the target nucleic acid. The contiguous bases are preferably at least about 80%, more preferably at least about 90%, and most preferably about 100% complementary to a region of the target nucleic acid sequence. The analogous oligonucleotide is preferably about 12 to 60 bases long and may optionally include modified bases.

A template-complementary amplification oligonucleotide has a region capable of hybridizing to the target nucleic acid at a position located 3' of the target sequence. The template-complementary oligonucleotide may contain a non-complementary region such as a 5' promoter region.

Preferably, the target-complementary oligonucleotide contains at least about 10 contiguous bases, and more preferably at least about 12 contiguous bases, which are complementary to a region of the target nucleic acid sequence. The contiguous bases are preferably at least about 80%, more preferably at least about 90%, and most preferably about 100% complementary to a region of the target sequence. The template-complementary oligonucleotide is preferably 12 to 60 nucleotide bases in length and optionally may include modified nucleotides.

A "primer" refers to an optionally modified oligonucleotide which is capable of hybridizing to a template and which has a 3' end that can be efficiently extended in a known polymerization reaction. The 5' region of the primer may be non-complementary to the target nucleic acid. If the 5' non-complementary region includes a promoter sequence, it is referred to as a "promoter-primer." A primer or promoter-primer may be analogous or complementary to a target nucleic acid.

Transcription-Associated Amplification

Transcription-associated amplification uses an RNA polymerase to produce multiple RNA transcripts from a nucleic acid template. Transcription-associated amplification generally employs an RNA polymerase, a DNA polymerase, deoxyribonucleoside triphosphates, ribonucleoside triphosphates, and a promoter-template complementary oligonucleotide. Often an analogous oligonucleotide is also used.

Different variations of transcription-associated amplification are well known in the art. Examples of different variations, which use different reaction conditions and different numbers and types of amplification oligonucleotides, are described in detail in Burg et al., U.S. Pat. No. 5,437,990; Kacian et al., U.S. Pat. Nos. 5,399,491 and 5,554,516; Kacian et al., PCT Int'l Pub. No. WO 93/22461; Gingeras et al., PCT Int'l Pub. No. WO 88/01302; Gingeras et al., PCT Int'l Pub. No. WO 88/10315; Malek et al., U.S. Pat. No. 5,130,238; Urdea et al., U.S. Pat. Nos. 4,868,105 and 5,124,246; McDonough et al., PCT Int'l Pub. No. WO 94/03472; and Ryder et al., PCT Int'l Pub. No. WO 95/03430.

Briefly, generally transcription-associated amplification uses a promoter-template complementary oligonucleotide containing a 5' base sequence region which, when made double-stranded, is recognized by an RNA polymerase (labeled "P" in FIG. 2), and a 3' sequence region capable of hybridizing to a template nucleic acid at a location 3' of a target sequence (as shown in FIG. 2, step (A)). After hybridization of the promoter-template complementary oligonucleotide and the template, a double-stranded promoter is formed upstream from the template. The double-stranded promoter may be formed by polymerase-mediated primer extension of the promoter-template complementary oligonucleotide to produce a target complementary strand (see FIG. 2, step (A)), followed by hybridization of an analogous oligonucleotide (e.g., primer 24 of FIG. 2, step (B)) and primer extension of the analogous oligonucleotide (see FIG. 2, step (B)). Other known techniques are suitable for forming a double-stranded promoter, such as those involving primer extension of the target nucleic acid.

Transcription-associated amplification proceeds with the binding of an enzyme having RNA polymerase activity to a promoter region and synthesis of single-stranded RNA transcripts in a 5' to 3' direction (see FIG. 2, step (C)). Multiple RNA transcripts (e.g., about 100 to 3,000), can be produced by transcription-associated amplification using a single template (e.g., by repeating steps (C) to (F)).

In a preferred embodiment, target amplification uses a transcription-associated amplification procedure that uses RNase H activity (e.g., supplied by reverse transcriptase) to generate large amounts of single-stranded nucleic acid in an essentially constant reaction condition.

Other Amplification Methods

Other well-known amplification procedures may be used in the amplification step of the methods of the present invention, including Replicase-Mediated Amplification, Polymerase Chain Reaction (PCR), and Ligase Chain Reaction (LCR). Replicase-mediated amplification uses self-replicating RNA molecules, and a replicase such as QB-replicase (e.g., see Kramer et al., U.S. Pat. No. 4,786,600, and PCT Int'l Pub. No. WO 90/14439). PCR amplification is well known and uses DNA polymerase, primers and thermal cycling to synthesize multiple copies of the two complementary strands of a DNA or cDNA (e.g., see Mullis et al., U.S. Pat. Nos. 4,683,195, 4,683,202, and 4,800,159; *Methods in Enzymology*, 1987, Vol. 155:335–350). LCR uses at least four separate oligonucleotides to amplify a target and its complementary strand by using multiple cycles of hybridization, ligation, and denaturation (as described in European Pat. App. Pub. No. 0 320 308).

Detection of Target Polynucleotide

The presence of a target polynucleotide can be detected using different techniques that use a detection probe and/or detect an amplified nucleic acid. Preferably, the target polynucleotide is detected using a labeled probe which hybridizes to the target polynucleotide or to an amplification product of the target polynucleotide, particularly an amplified nucleic acid that is complementary to the target polynucleotide.

Labeled probes may contain different types of labels and different techniques may be used to detect the label. For example, well known probe labels include radioisotopes, fluorescent moieties, chemiluminescent moieties, and catalytic groups (e.g., an enzyme which participates in a reaction resulting in a color change). Examples of production and/or use of such labeled probes are described in detail in Sambrook et al., *Molecular Cloning, A Laboratory Manual*, 2nd ed. (Cold Spring Harbor Laboratory Press, Cold Spring Habor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333; and Becker et al., European Pat. App. Pub. No. 0 747 706.

Labeled probes may be hybridized to a target polynucleotide, an amplified nucleic acid, or an intermediate molecule which is hybridized directly or indirectly to the target polynucleotide or amplified nucleic acid. Indirect hybridization may be accomplished by using multiple intermediate molecules hybridized together.

Amplified nucleic acid may be detected using a labeled probe or using other well known methods of detecting nucleic acid. For example, the amplified nucleic acid may be labeled during amplification by using labeled precursors or after amplificaiton using fluorescent intercalating agents (e.g., ethidium bromide). Labeled amplified nucleic acid may be detected using well known procedures, such as, for example, gel filtration, gel electrophoresis, and HPLC.

The following examples illustrate some preferred embodiments of the present invention, although those skilled in the art will appreciate that other reagents and reaction conditions may be used to equally practice the methods of the present invention.

EXAMPLE 1

Adjusting $T_m$ by Varying Complementarity Length

One method of adjusting the $T_m$ of a hybridization complex is to vary the length of complementarity between two nucleic acids making up the complex. This example illustrates changes in $T_m$ due to differences in the lengths of complementarity in a complex.

Hybrids were formed between a first and second oligonucleotide strands. The first strand was a homopolymer of 40 deoxythymidines ($dT_{40}$), and the second strand was a homopolymer of deoxyadenosines of varying sizes ($dA_n$). These oligonucleotides were synthesized using standard nucleic acid synthesis procedures.

Both strands (350 pmols each) were mixed in a 40 µL volume containing 20 µL of 2× Hybridization Buffer (200 mM lithium succinate (pH 5.1–5.2), 17% lithium lauryl sulfate (LLS), 3 mM ethylenediaminetetraacetic acid (EDTA), and 3 mM ethylene glycol N, N, N', N'-tetraacetic acid (EGTA)) and heated at 55° C. for 30 minutes. Then, each complex was diluted to 300 µl with 1× Hybridization Buffer (i.e., half the concentration of 2× Hybridization Buffer).

In this solution, $T_m$ was determined by detecting a hyperchromatic shift. Briefly, absorbance was measured at 260 nm during incremental changes in the temperature of the reaction mixture and a shift in the absorbance of the solution was detected over the temperature range. The $T_m$ is the temperature at the midpoint of the absorbance shift. Table 1 shows the results of hybridization complexes in which the $dA_n$ length varied over a range of $dA_{10}$ to $dA_{40}$.

TABLE 1

| Hybrid | $T_m$ |
| --- | --- |
| $dA_{40}$: $dT_{40}$ | 70.3° C. |
| $dA_{30}$: $dT_{40}$ | 68.4° C. |
| $dA_{25}$: $dT_{40}$ | 64.5° C. |
| $dA_{20}$: $dT_{40}$ | 61.5° C. |
| $dA_{15}$: $dT_{40}$ | 56.0° C. |
| $dA_{10}$: $dT_{40}$ | 50.4° C. |

As seen from these results, as the length of complementarity increased, the $T_m$ of the complex also increased. The longer hybridization complexes (e.g., $dA_{30}$: $dT_{40}$) tended to have relatively broad absorbance shifts because there are potentially many types of hybridization complexes in the mixture due to offset pairing (e.g., 30-mer, 29-mer, 28-mer pairing and so forth). The combinations of homopolymers that resulted in shorter hybridization complexes (e.g., $dA_{15}$:$dT_{40}$ which can form up to a 15-mer complex) had a $T_m$ below about 60° C.

This property was further examined by incubating 100 µg of immobilized poly-$dT_{14}$ or $dT_{30}$ probe attached to magnetic beads with 2.5 pmols of a $^{32}$P-labeled $dA_{30}$ capture probe in solution. Reactants were incubated in a hybridization buffer (3 mM EDTA, 3 mM EGTA, 17% LLS, 190 mM succinic acid, 250 mM lithium hydroxide, pH 5.1±0.1) for 30 min at either 60° C. or room temperature (about 25° C.) in five replicates for each hybridization condition. At room temperature, the average percentages of the labeled $dA_{30}$ probes hybridized to the $dT_{14}$ and $dT_{30}$ probes were 90% and 88%, whereas at 60° C. the average percentages of the labeled $dA_{30}$ probes hybridized to the $dT_{14}$ and $dT_{30}$ probes were 61% and 1%, respectively.

These hybridization characteristics were exploited in a two-step hybridization assay in which the immobilized probe was present during hybridization conditions at two different temperatures as demonstrated in the next example.

EXAMPLE 2

Two Step Hybridization

This example illustrates the two-step hybridization method using two hybridization temperatures to achieve target polynucleotide capture. In one assay condition, the capture probe, target polynucleotide and immobilized probe were concurrently in the admixture throughout both hybridization conditions. In another assay, the immobilized probe was added after hybridization of the capture probe to the target polynucleotide in the first hybridization condition. The concurrent admixture of the first assay is advantageous because it requires fewer reagent addition steps, but the separate addition of immobilized probe generally resulted in about a two-fold higher signal than seen for the two-step hybridization performed with the concurrent admixture.

The capture probe oligonucleotide and acridinium ester (AE)-labeled target polynucleotide were synthesized and detected using standard techniques. Such techniques are known in the art, as described in Sambrook et al., *Molecular Cloning, A Laboratory Manual, $2^{nd}$* ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; and Arnold et al., U.S. Pat. No. 5,283,174.

Capture probe (1.25 pmol) and AE-labeled target polynucleotide were initially incubated for 30 min at 60° C. in 1× Hybridization Buffer (see Example 1) with, or without, 100 µg of a poly-T immobilized probe attached to Seradyn magnetic beads, and then shifted to room temperature for 30 min. For samples incubated at 60° C. without the bead-attached immobilized probe, this component (in 50 µl 1× Hybridization Buffer) was added at the start of the second incubation. Volumes of both samples were kept the same by adding 50 µl 1× Hybridization Buffer to the assay that already contained immobilized probe. The immobilized probe was a homopolymer of $dT_{14}$ or $dT_{30}$ attached to the solid support which were magnetic beads. The capture probe was a polynucleotide had a base sequence complementary to a sequence in the target polynucleotide (a *Neisseria gonorrhoeae* 16S rRNA sequence) and a poly-A tail of $dA_{15}$ or $dA_{30}$. The target sequence was AE-labeled *N. gonorrhoeae* 16S rRNA. Using this combination, an immobilized probe-:capture probe:target polynucleotide complex was formed by hybridization of target sequence with the target complementary sequence of the capture probe during the first hybridization at 60° C., and hybridization of the dA region of the capture probe with the dT region of the immobilized probe during the second hybridization at room temperature.

The captured AE-labeled target polynucleotide was purified by applying a magnetic field to attract the beads with immobilized probe to a location on the reaction container, and then washing twice with Binding Buffer (50 mM lithium succinate, 100 mM LiCl, 1.5% LLS, 1.5 mM EDTA, 1.5 mM EGTA, pH 5.2). The beads were resuspended and captured target polynucleotide was detected by measuring chemiluminescence produced from the AE label. Chemiluminescence was detected as Relative Light Units (RLU) using techniques substantially as described previously (Arnold et al. *Clinical Chemistry* 35:1588–1594 (1989); Nelson et al., U.S. Pat. No. 5,658,737. The RLU results are presented in Table 2 are mean values of samples tested in triplicate.

TABLE 2

| Poly - T of Immobilized Probe | Poly - A of Capture Probe | Immobilized Probe Added Before Second Hybridization | Immobilized Probe Present During Both Hybridizations |
| --- | --- | --- | --- |
| $dT_{30}$ | $dA_{30}$ | 54,895[1] | 31,608 |
|  | $dA_{15}$ | 44,558 | 30,290 |
| $dT_{14}$ | $dA_{30}$ | 65,313[2] | 63,240 |

TABLE 2-continued

| Poly - T of Immobilized Probe | Poly - A of Capture Probe | Immobilized Probe Added Before Second Hybridization | Immobilized Probe Present During Both Hybridizations |
|---|---|---|---|
| | $dA_{15}$ | 43,285 | 37,479 |

[1]Represents capture of 62% of the labeled target.
[2]Represents capture of 67% of the labeled target.

The results of Table 2 show that a two step hybridization can be used to effectively capture the target polynucleotide using a capture probe and an immobilized probe which is either present in the reaction mixture during both hybridizations or added before the second hybridization. Thus, this method can achieve target capture when all reagents are concurrently present during both hybridizations, thus requiring fewer reagent addition steps. The results of Table 2 also show that relatively short complementary sequences ($dT_{14}$ and $dA_{15}$) were effective for target capture in the immobilized probe:capture probe:target polynucleotide complex. Use of the 14-mer immobilized probe resulted in substantially the same signal whether the immobilized probe was added at the second hybridization or was present during both hybridizations. A shorter immobilized probe homopolymer appeared to be more advantageous than a shorter capture probe homopolymer as seen by the higher signal obtained with the $dT_{14}$:$dA_{30}$ combination compared to the $dT_{30}$:$dA_{15}$ combination.

EXAMPLE 3

Two Step Hybridization with Amplified Target Sequence

This example shows that the two step hybridization method of the present invention can be used to detect a *Mycobacterium tuberculosis* target polynucleotide present in a clinical sample. The assay is also capable of detecting other Mycobacterium species (i.e., *M. bovis, M. simiae* and *M. africanum*, often referred to collectively as the *M. tuberculosis* complex) but, for the sake of simplicity, will be described herein with reference to *M. tuberculosis*.

The basic protocol included the following steps. A lysate of the sample was prepared by adding a clinical sample (e.g., 500 μl of sediment from sputum, bronchoalveolar lavage or bronchial washings) to an equal volume of a lysis buffer (2.2 M LiCl, 250 mM HEPES buffer, pH 7.5, containing 4% (w/v) LLS) and organisms in the lysate were heat killed (95° C. for 15 min). If *M. tuberculosis* is present in the clinical sample, a target polynucleotide (e.g., rRNA sequence) derived from *M. tuberculosis* will be present in the lysate. An aliquot (250 μl) of the lysate was mixed with an equal volume of a solution containing the capture probe specific for the *M. tuberculosis* target sequence and an immobilized probe attached to a solid support. The capture probe was a 58-base oligonucleotide containing a 5' 15-base sequence complementary to a *M. tuberculosis* is rRNA sequence, an internal $T_3$, and a 3'$dA_{40}$ tail. The immobilized probe was a poly-$dT_{14}$ sequence attached using carbodiimide chemistry (substantially as previously described by Lund, et al., *Nuc. Acids Res.* 16:10861–10880, 1988) to a solid support of magnetic particles (0.7–1.05 μ particles, Seradyn, Indianapolis, Ind.). In this assay, 5 pmol of the capture probe and 50 μg of immobilized probe particles were used per reaction. The mixture was incubated successively at two different temperatures (60° C. for 20 min, and 25° C. for 15 min). At the first temperature, the *M. tuberculosis*-complementary sequence of the capture probe hybridized to the target sequence because the $T_m$ of that hybridization complex is greater than 60° C., and at the second temperature the homopolymeric immobilized probe hybridized to the complementary homopolymeric region of the capture probe because the $T_m$ of the dA:dT complex is less than about 50° C. Following both incubations, the magnetic beads were separated from the solution using a magnetic field substantially as described in Example 2. If *M. tuberculosis* was present in the sample, these magnetic beads have attached a hybridization complex consisting of immobilized probe:capture probe:target polynucleotide. If *M. tuberculosis* was not present in the sample, the beads have attached a hybridization complex consisting of immobilized probe and capture probe. The beads were washed twice with 1 ml of washing buffer per wash by resuspending the beads in buffer and then repeating the magnetic separation step. Washed beads were then resuspended in 75 μl of a nucleic acid amplification reagent solution for transcription associated amplification using methods substantially as described in Kacian et al., U.S. Pat. Nos. 5,399,491 and 5,554,516. The beads and 15 pmol of each primer specific for the *M. tuberculosis* target polynucleotide were incubated in a reaction mixture (40 mM Trizma base, pH 7.5, 17.5 mM KCl, 20 mM $MgCl_2$, 5% polyvinylpyrrolidone (PVP), 1 mM each dNTP, 4 mM each rNTP), covered with a layer (200 μl) of inert oil to prevent evaporation, at 60° C. for 10–15 min, and then at 41.5–42° C. for 5 min. Reverse transcriptase (about 750 U and about 400 Units of T7 RNA polymerase in 25 μl) was added per reaction, mixed, and the amplification of the target polynucleotide proceeded at 41.5–42° C. for 2 hr. Amplified *M. tuberculosis* target sequences were detected using an AE-labeled probe which was detected as chemiluminescence and expressed in relative light units (RLU) substantially as described previously (U.S. Pat. No. 5,658,737 at column 25, lines 27–46; Nelson et al., 1996, *Biochem.* 35:8429–8438 at 8432). For each assay, a negative control consisting of all of the same reagents but substituting an equal volume of negative sputum for sample, and a positive control consisting of all of the same reagents but including 50 μl of extracted total cellular *M. tuberculosis* RNA (containing about 2000 copies of rRNA) instead of sample. Duplicate tests were perfomed (RLU No.1 and No.2 in Table 3).

The results of this assay on fifteen clinical samples that were independently determined to be positive for presence of *M. tuberculosis* (based on standard clinical smear analysis and/or BACTEC broth culture results) are presented in Table 3.

TABLE 3

| Sample No. | Smear Result | Culture Result | RLU No. 1 | RLU No. 2 |
|---|---|---|---|---|
| 1 | Positive | Unknown | $3.04 \times 10^6$ | $2.87 \times 10^6$ |
| 2 | Positive | Unknown | $3.09 \times 10^6$ | $2.99 \times 10^6$ |
| 3 | Positive | Unknown | $3.18 \times 10^6$ | $3.00 \times 10^6$ |
| 4 | Positive | Unknown | $3.28 \times 10^6$ | $3.23 \times 10^6$ |
| 5 | Positive | Positive | $2.97 \times 10^6$ | $3.04 \times 10^6$ |
| 6 | Positive | Positive | $3.16 \times 10^6$ | $2.94 \times 10^6$ |
| 7 | Unknown | Positive | $2.87 \times 10^6$ | $2.98 \times 10^6$ |
| 8 | Negative | Positive | $3.46 \times 10^4$ | $2.05 \times 10^6$ |
| 9 | Negative | Positive | $3.11 \times 10^6$ | $2.99 \times 10^6$ |
| 10 | Negative | Positive | $3.09 \times 10^6$ | $3.09 \times 10^6$ |
| 11 | Negative | Positive | $1.35 \times 10^6$ | $6.15 \times 10^5$ |
| 12 | Negative | Positive | $3.01 \times 10^6$ | $3.13 \times 10^6$ |
| 13 | Negative | Positive | $2.90 \times 10^6$ | $2.88 \times 10^6$ |
| 14 | Negative | Positive | $3.12 \times 10^6$ | $3.07 \times 10^6$ |
| 15 | Negative | Positive | $2.93 \times 10^6$ | $3.00 \times 10^6$ |

TABLE 3-continued

| Sample No. | Smear Result | Culture Result | RLU No. 1 | RLU No. 2 |
|---|---|---|---|---|
| Positive Controls | Not Applicable | Not Applicable | $2.98 \times 10^6$<br>$3.00 \times 10^6$ | $2.89 \times 10^6$ |
| Negative Controls | Not Applicable | Not Applicable | $3.45 \times 10^3$<br>$2.05 \times 10^3$ | $5.67 \times 10^3$ |

As can be seen from the results shown in Table 3, all of the samples that were positive for *M. tuberculosis* based on at least one clinical assay result, tested positive in the two step hybridization assay relative to the negative control. Positive results were based on samples having an RLU reading of at least about 10-fold greater than that of the negative control. For most samples, the positive result was based an RLU reading of at least about 100-fold greater than that of the negative control. Generally, the chemiluminescence indicative of *M. tuberculosis* target polynucleotide in the sample was about 1,000-fold greater than that detected in the negative control and essentially equal to or greater than that of the positive control.

EXAMPLE 4

Two Step Hybridization Assay for Detecting Varying Levels of a *Neisseria Gonorrhoeae* Target This example shows that the two-step hybridization method of the present invention can be used to detect as little as 5 fg of a target polynucleotide indicative of a bacterial infection. The target polynucleotide was a rRNA sequence specific to *N. gonorrhoeae* (Hogan et al., U.S. Pat. No. 5,541,308; Nelson et al., 1996, *Biochem.* 35:8429–8438). Moreover, the results were reproducible with little variation when the samples were stored over a three-day period at 0–4° C. and assayed on day 1, 2 and 3. The 5 fg and 50 fg amounts of *N. gonorrhoeae* target polynucleotide assayed correspond to rRNA present in 1 cell and 10 cells, respectively.

The basic protocol used includes the following steps. For each assayed sample, a 20 μl aqueous solution of either 0 fg (negative control), 5 fg or 50 fg of *N. gonorrhoeae* target polynucleotide in 400 μl of water was mixed with 400 μl of a synthetic urine control (KOVATROL™; Hycor Biomedical, Inc.) and 200 μl of a target capture buffer (TCB; consisting of 2.2 M LiCl, 250 mM HEPES buffer, pH 7.5) containing a capture oligonucleotide (6.25 nM) having a sequence complementary to the *N. gonorrhoeae* target polynucleotide and a $dT_3dA_{30}$ sequence. Immobilized $dT_{14}$ probe attached to magnetic particles as the solid support were added to 100 μg/ml and the mixture was incubated successively at two different temperatures (60° C. for 20 min, and 25° C. for 15 min). At the first temperature, the capture probe and the target polynucleotide hybridized because the $T_m$ of the capture probe:target polynucleotide complex is greater than 60°, and at the second temperature the immobilized probe and the poly-dA portion of the capture probe hybridized because the $T_m$ of the dA:dT complex is less than about 52° C. Following incubation, the magnetic beads were separated from the solution using a magnetic field substantially as described in Example 2. For samples containing the *N. gonorrhoeae* target polynucleotide, the magnetic beads have attached the immobilized probe:capture probe:target polynucleotide complex, whereas for the negative control sample the beads have attached the immobilized probe:capture probe. Then the beads were washed twice substantially as described in Example 3 and the washed beads were resuspended in 75 μl of a nucleic acid amplification reagent and amplified substantially as described in Example 3 using a primer specific for the *N. gonorrhoeae* target polynucleotide. After amplification, the amplified target sequences were detected using a AE-labeled which was detected using a chemiluminescent assay as described in Example 3, and the signal was expressed in relative light units (RLU). For each day's assays, background RLU of the negative controls and positive controls were determined in the same manner using the same reagents. Results of the assays are shown in Table 4, including RLU results for each experimental sample, and the mean values of two positive controls and ten negative controls obtained for each day. The background (mean of two samples) values were $6.81 \times 10^2$, $1.18 \times 10^3$ and $6.61 \times 10^2$ RLU for days 1, 2 and 3 respectively.

TABLE 4

| Sample | Target (fg) | Day 1 RLU | Day 2 RLU | Day 3 RLU |
|---|---|---|---|---|
| 1 | 5 | $7.78 \times 10^5$ | $6.46 \times 10^5$ | $6.95 \times 10^5$ |
| 2 | 5 | $7.73 \times 10^5$ | $7.08 \times 10^5$ | $7.06 \times 10^5$ |
| 3 | 5 | $8.30 \times 10^5$ | $7.00 \times 10^5$ | $6.57 \times 10^5$ |
| 4 | 5 | $7.69 \times 10^5$ | $7.34 \times 10^5$ | $7.60 \times 10^5$ |
| 5 | 5 | $7.73 \times 10^5$ | $7.76 \times 10^5$ | $7.95 \times 10^5$ |
| 6 | 5 | $7.01 \times 10^5$ | $6.47 \times 10^5$ | $7.14 \times 10^5$ |
| 7 | 5 | $7.32 \times 10^5$ | $6.70 \times 10^5$ | $7.63 \times 10^5$ |
| 8 | 5 | $7.84 \times 10^5$ | $7.23 \times 10^5$ | $7.06 \times 10^5$ |
| 9 | 5 | $7.45 \times 10^5$ | $7.17 \times 10^5$ | $7.18 \times 10^5$ |
| 10 | 5 | $7.45 \times 10^5$ | $7.11 \times 10^5$ | $7.68 \times 10^5$ |
| 11 | 50 | $8.58 \times 10^5$ | $7.51 \times 10^5$ | $7.57 \times 10^5$ |
| 12 | 50 | $8.20 \times 10^5$ | $4.61 \times 10^5$ | $7.77 \times 10^5$ |
| 13 | 50 | $7.66 \times 10^5$ | $6.99 \times 10^5$ | $7.21 \times 10^5$ |
| 14 | 50 | $7.85 \times 10^5$ | $7.97 \times 10^5$ | $7.45 \times 10^5$ |
| 15 | 50 | $8.17 \times 10^5$ | $7.80 \times 10^5$ | $7.76 \times 10^5$ |
| 16 | 50 | $7.98 \times 10^5$ | $7.33 \times 10^5$ | $7.42 \times 10^5$ |
| 17 | 50 | $7.51 \times 10^5$ | $7.36 \times 10^5$ | $7.41 \times 10^5$ |
| 18 | 50 | $7.76 \times 10^5$ | $8.01 \times 10^5$ | $7.80 \times 10^5$ |
| 19 | 50 | $7.24 \times 10^5$ | $7.27 \times 10^5$ | $7.62 \times 10^5$ |
| 20 | 50 | $7.74 \times 10^5$ | $7.54 \times 10^5$ | $7.70 \times 10^5$ |
| Negatives (10) | 0 | 201 | −218 | 74 |

The results presented in Table 4 show that the two step hybridization assay is capable of reproducibly detecting as little as 5 fg of an *N. gonorrhoeae* target polynucleotide, producing chemiluminescence significantly above that of a samples containing no target polynucleotide tested under the same conditions. Moreover, when samples were stored and retested using the method over the course of three days there was good reproducibility of the results over the entire time period. The results also show good sample-to-sample reproducibility over the three-day period.

EXAMPLE 5

Two-Step Hybridization Assay for Detecting Bacterial In Clinical Urine Samples

This example shows that the two-step hybridization method of the present invention can be used to detect a target indicative of a bacterial infection using clinical urine samples. The target polynucleotide was a sequence specific to *Chlamydia trachomatis*. The samples had been independently tested for *C. trachomatis* using a PCR-based assay and the results obtained with the two-step hybridization method were compared to those obtained with the PCR-based assay. The urine samples were tested in duplicate using the two-step hybridization method, with the samples arranged in a random order relative to their classification (positive or negative) based on their PCR-based assay results.

Briefly, the two-step hybridization assay protocol was as follows. Each reaction tube contained 200 µl of TCB (as defined in Example 4) containing 6.25 pmols of a capture oligonucleotide having a sequence complementary to the *C. trachomatis* target polynucleotide and a $dT_3dA_{30}$ sequence, into which was added 800 µl of prepared urine sample (400 µl urine plus 400 µl TM buffer (100 mM $(NH_4)_2SO_4$, 50 mM Hepes, pH 7.5, 8% LLS)) or 800 µl of controls (negative controls were 400 µl KOVATROL™ plus 400 µl TM buffer; positive controls were 400 µl KOVATROL™ plus 400 µl TM buffer containing 5 fg of a *C. trachomatis* total cellular RNA (i.e., rRNA target polynucleotide). The tubes were sealed, mixed, and incubated at 60° C. for 30 min, and then at 40° C. for 30 min. The tubes were then subjected to a magnetic field and the magnetic beads with immobilized probe were separated from the solution, and the immobilized components were washed twice substantially as described in Example 2. At 60° C., the capture probe and the *C. trachomatis* target polynucleotide hybridized because the $T_m$ of the capture probe:target polynucleotide complex is greater than 60° C., and at the second temperature the immobilized poly-dT probe and the poly-A portion of the capture probe hybridized because the $T_m$ of the dA:dT complex is less than about 52° C. The target polynucleotide was amplified using a primer specific for the *C. trachomatis* target sequence and reagents for transcription-associated amplification contained in a volume of 75 µl substantially as described in Example 3 except that amplification was for 1 hr. The AE-labeled probe (100 µl) specific for the *C. trachomatis* target sequence was added, mixed, and the mixture incubated at 60° C. for 20 min, after which RLU were detected substantially as described in Example 3.

Table 5 shows the results of the two-step hybridization assays ("RLU" is the mean of the duplicate tests for 30 urine samples, and the means of the five positive and five negative controls) and PCR-based tests (positive or negative for detection of *C. trachomatis* nucleic acid).

tively high background signal. Thus, the two-step hybridization assay can be used to detect bacteria present in clinical urine samples, and provide positive or negative results comparable to those obtained with a PCR-based assay.

EXAMPLE 6

Two Step Hybridization Assay for Detecting Multiple Bacterial Targets in a Sample This example shows that the two-step hybridization method of the present invention can be used to detect multiple targets indicative of bacterial infections by different species in a single sample. The target polynucleotides were sequences specific to *Neisseria gonorrhoeae* and *Chlamydia trachomatis* and the assays were performed substantially as described in Examples 3–6. These samples were also spiked with a contaminant (1% to 10% v/v blood).

The assays were performed substantially as described in Examples 3–6, where the samples consisted of normal urine (no bacterial contamination) that contained either: no target polynucleotide (negative controls); 5 fg of a *C. trachomatis* target polynucleotide; 5 fg of a *N. gonorrhoeae* target polynucleotide; or a mixture of 5 fg of a *C. trachomatis* target polynucleotide and 5 fg of a *N. gonorrhoeae* target polynucleotide. For each set of samples, the assay tubes further included either 0%, 1%, 5% or 10% v/v blood. Simultaneous detection of the two target sequences using chemiluminescent probes was substantially as described by Nelson et al. (1996, *Biochem.* 35:8429–8438 at 8432) using an ortho-F-AE labeled probe specific for the *C. trachomatis* target polynucleotide and a 2-Me-AE labeled probe specific for the *N. gonorrhoeae* target polynucleotide. The urine samples were prepared and incubated at 60° C. for 30 min, and then at 40° C. for 30 min for the successive hybridization steps substantially as described in Example 5 herein, except that the blood contaminant was included in some of the samples as described above. The immobilized probes in

TABLE 5

| Sample No. | PCR Results | RLU | Sample No. | PCR Results | RLU |
|---|---|---|---|---|---|
| 1 | Positive | $4.42 \times 10^5$ | 17 | Negative | 0 |
| 2 | Negative | $1.66 \times 10^3$ | 18 | Positive | $3.59 \times 10^5$ |
| 3 | Positive | $2.95 \times 10^5$ | 19 | Positive | $3.64 \times 10^5$ |
| 4 | Negative | 0 | 20 | Positive | $3.51 \times 10^5$ |
| 5 | Positive | $1.62 \times 10^5$ | 21 | Positive | $3.75 \times 10^5$ |
| 6 | Positive | $4.15 \times 10^5$ | 22 | Negative | $9.15 \times 10^3$ |
| 7 | Positive | $5.76 \times 10^5$ | 23 | Positive | $3.21 \times 10^5$ |
| 8 | Negative | $3.69 \times 10^3$ | 24 | Negative | 0 |
| 9 | Positive | $4.45 \times 10^5$ | 25 | Positive | $4.59 \times 10^5$ |
| 10 | Negative | 0 | 26 | Negative | 8 |
| 11 | Positive | $5.00 \times 10^5$ | 27 | Positive | $3.07 \times 10^5$ |
| 12 | Negative | 0 | 28 | Positive | $3.52 \times 10^5$ |
| 13 | Negative | 0 | 29 | Negative | 0 |
| 14 | Negative | 0 | 30 | Negative | 0 |
| 15 | Negative | 0 | Positive Controls | Not Applicable | $3.14 \times 10^5$ |
| 16 | Negative | 0 | Negative Controls | Not Applicable | 0 |

As can be seen from the results of Table 5, in all samples assayed, the two-step hybridization method provided positive results for those samples that had independently tested positive using a PCR-based assay, and in all cases that tested negative using the PCR-based assay, the sample was also negative when assayed by the two-step hybridization method. For those negative samples that had relatively high ($10^3$) negative signal (samples 2, 8 and 22), the duplicate assays always included one "0" RLU signal and one relahybridization complexes were purified using the magnetic field and washing steps, and the purified target sequences were amplified using transcription-associated amplification procedures that included primers specific for the *C. trachomatis* target polynucleotide and the *N. gonorrhoeae* target polynucleotide as described in Examples 4 and 5 above. The detection reagent was added and simultaneous chemiluminescence was detected from the *C. trachomatis*-specific labeled probe the *N. gonorrhoeae*-specific labeled probe. For each type of sample assayed, four replicates were assayed and the RLU results (mean values for each type of sample) are presented in Table 6. In Table 6, the signal (RLU) detected for the *C. trachomatis*-specific labeled probe is indicated by "CT" and the signal detected for the *N. gonorrhoeae*-specific labeled probe is indicated by "NG."

TABLE 6

|  | Negative Control | C. trachomatis Target | N. gonorrhoeae Target | C. trachomatis + N. gonorrhoeae Target |
|---|---|---|---|---|
| No Blood | CT: 1 NG: $1.86 \times 10^2$ | CT: $2.18 \times 10^5$ NG: $4.05 \times 10^2$ | CT: $4.90 \times 10^3$ NG: $9.37 \times 10^5$ | CT: $2.22 \times 10^5$ NG: $9.37 \times 10^5$ |
| 1% Blood | CT: 52 NG: $4.41 \times 10^2$ | CT: $2.73 \times 10^5$ NG: $1.38 \times 10^3$ | CT: $4.64 \times 10^3$ NG: $9.54 \times 10^5$ | CT: $1.73 \times 10^5$ NG: $9.80 \times 10^5$ |
| 5% Blood | CT: 27 NG: $4.42 \times 10^2$ | CT: $1.91 \times 10^5$ NG: $1.66 \times 10^3$ | CT: 0 NG: $1.06 \times 10^6$ | CT: $1.65 \times 10^5$ NG: $9.19 \times 10^5$ |
| 10% Blood | CT: 14 NG: $1.36 \times 10^2$ | CT: $2.13 \times 10^5$ NG: $1.85 \times 10^3$ | CT: 0 NG: $1.05 \times 10^6$ | CT: $1.35 \times 10^5$ NG: $1.12 \times 10^6$ |

The results presented in Table 6 show that the two-step hybridization assay can be used to detect two targets in a single sample simultaneously. The negative controls gave essentially negligible signals compared to those of the samples that contained the *C. trachomatis* target alone, the *N. gonorrhoeae* target alone, or the combined targets. Detection of either tar3get was not interfered with by up to 10% v/v blood contamination, and both targets were detected simultaneously in a single sample even with blood contamination up to 10% v/v.

EXAMPLE 7

Two Step Hybridization to Capture the Target Polynucleotide with a Primer for Amplification This example demonstrates capture of a target polynucleotide (HIV-1 RNA) using a two-step hybridization procedure in which the mixture includes a magnetic particles with immobilized $dT_{14}$ probes, a capture probe having a 3' $dA_{30}$ covalently linked to a sequence specific for the HIV-1 target polynucleotide, and a promoter primer made up of a 5' T7 promoter sequence covalently linked to an HIV-1 specific target binding sequence. The mixture, in an aqueous buffer (e.g., 300 mM HEPES, pH 7.5, 2.5 mM EDTA, 7% LLS), includes HIV-1 RNA at 0 to $10^5$ copies per reaction (e.g., $10^2$, $10^3$, $10^4$, and $10^5$ copies per reaction, with 0 copies in the negative control), the capture probe at 1.75 pmol/reaction, the promoter primer at 0.5–1 pmol/reaction and the immobilized probes on particles (substantially as described in Example 3) at 1 $\mu g/\mu l$. The mixture is incubated successively at two different hybridization conditions (60–65° C. for 15–20 min, and 25–30° C. for 15 min). Then the magnetic beads are immobilized by applying a magnetic field to the outside of the reaction container and the beads are washed three times at room temperature, substantially as described in Examples 3 and 4. Following removal of the last washing solution, the beads with the attached immobilized hybridization complex containing the HIV-1 target RNA and T7 promoter primer are added to an amplification reaction mixture containing an additional 3–5 pmol of the same T7 promoter primer that was included in the target capture hybridization and about 5 pmol of a second primer oligonucleotide that specifically hybridizes to the complementary strand synthesized from the HIV-1 template using the T7 promoter primer to initiate synthesis, at a location about 80 nt downstream from the T7 promoter primer binding site on the HIV-1 target sequence. The amplification reaction mixture containing salts and amplification substrates and enzymes, substantially as described in Example 3, is incubated at 42° C. for 2 hr to perform a transcription mediated amplification (substantially as described in Kacian et al., U.S. Pat. Nos. 5,399,491 and 5,554,516). After amplification, the amplified RNA transcripts are detected in a homogeneous detection assay by using an AE-labeled probe that specifically hybridizes to an HIV-1 sequence located between the two primers used in the amplification reaction (i.e., about 56 nt downstream of the T7 promoter primer binding site on the HIV-1 target sequence), using conditions substantially as described in Example 3 to detect the chemiluminescence. Amplified sequences are detected by an RLU signal significantly greater than obtained for the negative control for reaction mixtures initially containing at least $10^3$ copies of HIV-1 target RNA.

While several embodiments of the present invention have been described herein, various modifications to the particular probes may be made without departing from the spirit and scope of the present invention which is defined by the claims that follow.

We claim:

1. A method for amplifying a target polynucleotide that is present in a sample, comprising the steps of:
   a. providing a capture probe that hybridizes specifically to a target polynucleotide present in a sample;
   b. providing a first primer oligonucleotide that hybridizes specifically to the target polynucleotide at a location different than the location that the capture probe hybridizes to the target polynucleotide;
   c. mixing the capture probe and the primer oligonucleotide with a sample suspected of containing the target polynucleotide at a first hybridization condition that favors hybridization of the capture probe to the target polynucleotide and the primer oligonucleotide to the target polynucleotide, thereby producing a capture probe:target polynucleotide:primer oligonucleotide complex formed by hybridization of the capture probe and the primer oligonucleotide to the target polynucleotide, wherein the first hybridization condition disfavors hybridization of an immobilized probe and the capture probe;
   d. providing an immobilized probe that hybridizes specifically to the capture probe at a second hybridization condition that is different from the first hybridization condition;
   e. incubating a mixture containing the capture probe:target polynucleotide:primer oligonucleotide complex and the immobilized probe at a second hybridization condition that favors hybridization of the immobilized probe and the capture probe, thereby producing a captured target polynucleotide complex consisting essentially of an immobilized probe:capture probe:target polynucleotide:primer oligonucleotide complex formed by hybridization of the immobilized probe to the capture probe in the capture probe:target polynucleotide:primer oligonucleotide complex;
   f. purifying the captured target polynucleotide complex from other sample components by washing the captured target polynucleotide complex, thereby producing a purified target polynucleotide retained in the immobilized probe:capture probe:target polynucleotide:primer oligonucleotide complex; and
   g. then amplifying a base sequence in the target polynucleotide by initiating nucleic acid polymerization from the first primer oligonucleotide using the target polynucleotide as a template and a DNA polymerase activity, thereby producing an amplified nucleic acid.

2. The method of claim 1, wherein the first hybridization condition uses an incubation temperature below a $T_m$ of the capture probe:target polynucleotide hybridization complex and above a $T_m$ of the immobilized probe:capture probe hybridization complex, and wherein the second hybridization condition uses an incubation temperature below a $T_m$ of the immobilized probe:capture probe hybridization complex.

3. The method of claim 1, wherein the amplifying step further includes hybridizing a second primer oligonucleotide to the target polynucleotide upstream of the first primer oligonucleotide hybridized to the target polynucleotide, and polymerizes a first complementary nucleic acid strand initiating from the first primer oligonucleotide and a second complementary nucleic acid strand initiating from the second primer oligonucleotide, both complementary nucleic acid strands polymerized using the same strand of the target polynucleotide as a template.

4. The method of claim 3, wherein the second complementary nucleic acid strand displaces the first complementary nucleic acid strand from the target polynucleotide.

5. The method of claim 1, wherein the DNA polymerase activity is provided by a reverse transcriptase.

6. The method of claim 1, wherein the first primer oligonucleotide is a promoter primer.

7. The method of claim 1, wherein hybridization of the capture probe to the target polynucleotide and hybridization of the primer oligonucleotide to the target polynucleotide occurs in liquid phase.

8. The method of claim 1, wherein the amplifying step initiates polymerization from the first primer oligonucleotide hybridized to the target polynucleotide without releasing the target polynucleotide from the immobilized probe-:capture probe:target polynucleotide:primer oligonucleotide complex.

9. A method for amplifying a target polynucleotide that is present in a sample, comprising the steps of:
   a. providing a capture probe that hybridizes specifically to a target polynucleotide present in a sample;
   b. providing a first primer oligonucleotide that hybridizes specifically to the target polynucleotide at a location different than the location that the capture probe hybridizes to the target polynucleotide;
   c. mixing the capture probe and the primer oligonucleotide with a sample suspected of containing the target polynucleotide at a first hybridization condition that favors hybridization of the capture probe and the target polynucleotide, thereby producing a capture probe:target polynucleotide:primer oligonucleotide complex formed by hybridization of the capture probe and the primer oligonucleotide to the target polynucleotide, wherein the first hybridization condition disfavors hybridization of an immobilized probe and the capture probe and disfavors hybridization of the primer oligonucleotide to the target polynucleotide;

d. providing an immobilized probe that hybridizes specifically to the capture probe at a second hybridization condition that is different from the first hybridization condition;

e. incubating a mixture containing the capture probe:target polynucleotide complex and the primer oligonucleotide and immobilized probe at a second hybridization condition that favors hybridization of the immobilized probe with the capture probe and the primer oligonucleotide with the target polynucleotide, thereby producing a captured target polynucleotide complex consisting essentially of an immobilized probe:capture probe:target polynucleotide:primer oligonucleotide complex formed by hybridization of the immobilized probe with the capture probe which is hybridized with the target polynucleotide and the primer oligonucleotide with the target polynucleotide which is hybridized to the capture probe;

f. purifying the captured target polynucleotide complex from other sample components by washing the captured target polynucleotide complex, thereby producing a purified target polynucleotide retained in the immobilized probe:capture probe:target polynucleotide:primer oligonucleotide complex; and g. then amplifying a base sequence in the target polynucleotide by initiating nucleic acid polymerization from the first primer oligonucleotide using the target polynucleotide as a template and a DNA polymerase activity, thereby producing an amplified nucleic acid.

10. The method of claim 9, wherein the first hybridization condition uses an incubation temperature below a $T_m$ of the capture probe:target polynucleotide hybridization complex and above a $T_m$ of the immobilized probe:capture probe hybridization complex, and wherein the second hybridization condition uses an incubation temperature below a $T_m$ of the immobilized probe:capture probe hybridization complex.

11. The method of claim 9, wherein the amplifying step further includes hybridizing a second primer oligonucleotide to the target polynucleotide upstream of the first primer oligonucleotide hybridized to the target polynucleotide, and polymerizes a first complementary nucleic acid strand initiating from the first primer oligonucleotide and a second complementary nucleic acid strand initiating from the second primer oligonucleotide, both complementary nucleic acid strands polymerized using the same strand of the target polynucleotide as a template.

12. The method of claim 11, wherein the second complementary nucleic acid strand displaces the first complementary nucleic acid strand from the target polynucleotide.

13. The method of claim 9, wherein the DNA polymerase activity is provided by a reverse transcriptase.

14. The method of claim 9, wherein the first primer oligonucleotide is a promoter primer.

15. The method of claim 9, wherein the amplifying step initiates polymerization from the first primer oligonucleotide hybridized to the target polynucleotide without releasing the target polynucleotide from the immobilized probe:capture probe:target polynucleotide:primer oligonucleotide complex.

16. A method for detecting the presence of a target polynucleotide in a sample, comprising the steps of:

a. providing a capture probe that hybridizes specifically to a target polynucleotide present in a sample;

b. providing a first primer oligonucleotide that hybridizes specifically to the target polynucleotide at a location different than the location that the capture probe hybridizes to the target polynucleotide;

c. mixing the capture probe and the primer oligonucleotide with a sample suspected of containing the target polynucleotide to produce a mixture;

d. incubating the mixture at a first hybridization condition that favors hybridization of the capture probe to the target polynucleotide, thereby producing a capture probe:target polynucleotide complex formed by hybridization of the capture probe and the primer oligonucleotide to the target polynucleotide, wherein the first hybridization condition optionally favors hybridization of the primer oligonucleotide to the target polynucleotide and disfavors hybridization of an immobilized probe and the capture probe;

e. providing an immobilized probe that hybridizes specifically to the capture probe at a second hybridization condition that is different from the first hybridization condition;

f. incubating a mixture containing the capture probe:target polynucleotide complex and the immobilized probe at a second hybridization condition that favors hybridization of the immobilized probe and the capture probe and favors hybridization of the primer oligonucleotide with the target polynucleotide, thereby producing a captured target polynucleotide complex consisting essentially of an immobilized probe:capture probe:target polynucleotide:primer oligonucleotide complex formed by hybridization of the immobilized probe to the capture probe in the capture probe:target polynucleotide complex and the capture probe:target polynucleotide:primer oligonucleotide complex;

g. purifying the captured target polynucleotide complex from other sample components by washing the captured target polynucleotide complex, thereby producing a purified target polynucleotide retained in the immobilized probe:capture probe:target polynucleotide:primer oligonucleotide complex;

h. then amplifying a base sequence in the target polynucleotide by initiating nucleic acid polymerization from the first primer oligonucleotide using the target polynucleotide as a template and a DNA polymerase activity, thereby producing an amplified nucleic acid; and i. detecting the amplified nucleic acid which indicates the presence of the target polynucleotide in the sample.

17. The method of claim 16, wherein the detecting step detects an amplified nucleic acid that is complementary to a sequence in the target polynucleotide.

18. The method of claim 16, wherein the detecting step uses a labeled probe to detect the amplified nucleic acid in a homogeneous detection method.

19. The method of claim 16, wherein the capture probe is an oligonucleotide containing a target polynucleotide-binding region that is substantially complementary to a sequence in the target polynucleotide, and an immobilized probe-binding region that is substantially complementary to the immobilized probe.

20. The method of claim 16, wherein the amplifying step uses a transcription-associated amplification in which a reverse transcriptase acts together with the first primer oligonucleotide which is a promoter-primer to form a DNA duplex specific for the target polynucleotide and containing a double-stranded promoter, and then an RNA polymerase recognizes the double-stranded promoter to generate multiple RNA transcripts specific for the target polynucleotide, thereby producing the amplified nucleic acid.

* * * * *